US011761021B2

(12) United States Patent
Liu et al.

(10) Patent No.: US 11,761,021 B2
(45) Date of Patent: Sep. 19, 2023

(54) **RECOMBINANT *BACILLUS SUBTILIS* FOR SYNTHESIZING LACTO-N-NEOTETRAOSE AND APPLICATION THEREOF**

(71) Applicants: BRIGHT DAIRY & FOOD CO., LTD., Shanghai (CN); Jiangnan University, Wuxi (CN)

(72) Inventors: Long Liu, Wuxi (CN); Jian Chen, Wuxi (CN); Miao Wang, Wuxi (CN); Guocheng Du, Wuxi (CN); Xiaomin Dong, Wuxi (CN); Xueqin Lv, Wuxi (CN); Jianghua Li, Wuxi (CN)

(73) Assignees: JIANGNAN UNIVERSITY, Wuxi (CN); BRIGHT DAIRY & FOOD CO., LTD., Shanghai (CN)

( * ) Notice: Subject to any disclaimer, the term of this patent is extended or adjusted under 35 U.S.C. 154(b) by 620 days.

(21) Appl. No.: 16/747,016

(22) Filed: Jan. 20, 2020

(65) Prior Publication Data

US 2020/0140894 A1    May 7, 2020

(30) Foreign Application Priority Data

Feb. 27, 2019  (CN) .......................... 201910146431.1

(51) Int. Cl.
| | |
|---|---|
| *C12N 15/90* | (2006.01) |
| *C12P 19/44* | (2006.01) |
| *C12N 5/00* | (2006.01) |
| *C12N 1/20* | (2006.01) |
| *C12R 1/125* | (2006.01) |

(52) U.S. Cl.
CPC ............. *C12N 15/90* (2013.01); *C12N 1/205* (2021.05); *C12N 5/0018* (2013.01); *C12P 19/44* (2013.01); *C12N 2500/12* (2013.01); *C12N 2500/32* (2013.01); *C12N 2500/34* (2013.01); *C12N 2500/74* (2013.01); *C12R 2001/125* (2021.05)

(58) Field of Classification Search
CPC ...... C12N 15/90; C12N 1/205; C12N 5/0018; C12N 2500/12; C12N 2500/32; C12N 2500/34; C12N 2500/74; C12P 19/44; C12R 2001/125
See application file for complete search history.

(56) References Cited

U.S. PATENT DOCUMENTS

2012/0208181 A1*  8/2012  Merighi .................. C12P 19/18
                                                      536/123

OTHER PUBLICATIONS

Priem B et al. A new fermentation process allows large-scale production of human milk oligosaccharides by metabolically engineered bacteria. 2002. Glycobiology. vol. 12, No. 4. p. 235-240. (Year: 2002).*

* cited by examiner

*Primary Examiner* — Paul J Holland
(74) *Attorney, Agent, or Firm* — IPRO, PLLC

(57) ABSTRACT

The disclosure discloses recombinant *Bacillus subtilis* for synthesizing e lacto-N-neotetraose yield. The recombinant *Bacillus subtilis* is obtained by integrating two β-1,4-galactotransferase genes on a genome of a host bacterium *Bacillus subtilis* 168ΔamyE:$P_{43}$-lacY, $P_{43}$-lgtB, $P_{xylA}$-comK and exogenously expressing a β-1,3-N-glucosaminotransferase gene. Compared with a strain before transformation, the recombinant *Bacillus subtilis* of the disclosure improves the yield of the synthesized lacto-N-neotetraose from 720 mg/L to 1300 mg/L, laying a foundation for further metabolic engineering transformation of *Bacillus subtilis* for producing the lacto-N-neotetraose.

13 Claims, 2 Drawing Sheets

Specification includes a Sequence Listing.

RECOMBINANT *BACILLUS SUBTILIS* FOR SYNTHESIZING LACTO-N-NEOTETRAOSE AND APPLICATION THEREOF

TECHNICAL FIELD

The disclosure belongs to the technical field of genetic engineering, and particularly relates to recombinant *Bacillus subtilis* for synthesizing lacto-N-neotetraose and application thereof.

BACKGROUND

Breast milk is a natural and ideal food for babies. In breast milk, in addition to nutrients needed for infant growth and development, it also contains thousands of biologically active substances. The Human Milk Oligosaccharides (HMOs) is about 5-15 g/L in breast milk, and is the most important bifidus factor in breast milk. Lacto-N-neotetraose (LNnT) is an important component of HMOs, and it is also the core structural element of other complex breast milk oligosaccharides, such as fucosylated and sialylated oligosaccharides. Because lacto-N-neotetraose and its derivatives have important physiological functions such as promoting cell differentiation, improving the immune regulating function of intestinal epithelial cells, and increasing the relative abundance of intestinal probiotics, it is of great significant to synthesize the lacto-N-neotetraose. By using metabolic engineering in biosynthesis technology to construct an efficient synthesis system in *Bacillus subtilis*, not only can LNnT be produced in large scale industrially to meet demands, but also a chassis cell of a food-grade safe strain *Bacillus subtilis* producing breast milk oligosaccharides is constructed to provide support for the later synthesis of other breast milk oligosaccharides in *Bacillus subtilis*.

*Bacillus subtilis* is a generally regard as safe (GRAS) strain, has a clear genetic background, is easy for heterologous gene expression, has a short culture period and does not generate endotoxin. Therefore, construction of *Bacillus subtilis* engineering bacteria by metabolic engineering is an effective strategy for the production of lacto-N-neotetraose. However, due to insufficient activity of key enzymes in the synthetic pathway, the synthesis of the final yield is limited. It is urgent to solve the problem of how to improve the catalytic activity of the key enzymes and remove the limiting factors.

SUMMARY

To solve the above technical problems, the disclosure provides recombinant *Bacillus subtilis* for synthesizing lacto-N-neotetraose, and a construction method and application thereof.

Specifically, in a first aspect, the disclosure provides recombinant *Bacillus subtilis* for synthesizing lacto-N-neotetraose yield. The recombinant *Bacillus subtilis* is obtained by integrating two β-1,4-galactotransferase genes on a genome of the host bacterium *Bacillus subtilis* 168ΔamyE: $P_{43}$-lacY, $P_{43}$-lgtB, $P_{xylA}$-comK and exogenously expressing the β-1,3-N-glucosaminotransferase gene.

According to the disclosure, the expression of the β-1,4-galactotransferase is increased by increasing two copy numbers of β-1,4-galactotransferase genes in the genome, thereby increasing the enzyme activity, accelerating precursor transformation, and significantly increasing the yield of lacto-N-neotetraose.

It should be further explained that the host bacterium is obtained by using *Bacillus subtilis* 168 as a starting strain by regulating the expression of a gene comK by a promoter $P_{xylA}$, integrating a lactose permease-encoding gene onto an amyE site of the genome, and integrating a β-1,4-galactotransferase-encoding gene between a ydeS site and a ydzO site of the genome.

In a second aspect, the disclosure further provides a method for constructing the recombinant *Bacillus subtilis* for synthesizing lacto-N-neotetraose, including the following steps:

(1) constructing a recombinant fragment containing homologous arms of ydaH and ydzA genes, a β-1,4-galactotransferase gene, a $P_{43}$ promoter, and a bleomycin resistance gene sequence by fusion PCR;

(2) constructing a recombinant fragment containing homologous arms of yszA and ysxE genes, a β-1,4-galactotransferase gene, a $P_{43}$ promoter, and a chloramphenicol resistance gene sequence by fusion PCR;

(3) transforming the recombinant fragment constructed in step (1) into *Bacillus subtilis* 168ΔamyE:$P_{43}$-lacY, $P_{43}$-lgtB, PxylA-comK, and verifying to obtain recombinant *Bacillus subtilis* BY03a;

(4) transforming the recombinant fragment constructed in step (2) into the recombinant *Bacillus subtilis* BY03a of step (3), and verifying to obtain recombinant *Bacillus subtilis* BY03b;

(5) transforming pP43NMK-lgtA into the recombinant *Bacillus subtilis* BY03b to obtain recombinant *Bacillus subtilis* BY05 for synthesizing lacto-N-neotetraose.

According to the construction method of the disclosure, two copy numbers of β-1,4-galactotransferase genes are increased in a genome. The increased first copy number of β-1,4-galactotransferase-encoding gene lgtB is integrated between a ydaH site and a ydzA site. The increased second copy number of β-1,4-galactotransferase-encoding gene lgtB is integrated between a yszA site and a ysxE site.

Further, in step (1), the left homologous arm of the ydaH gene and the right homologous arm of the ydzA gene are used.

Further, in step (2), the left homologous arm of the yszA gene and the right homologous arm of the ysxE gene are used.

Further, the sequence of the recombinant fragment constructed in step (1) is shown in SEQ ID NO.47, and the sequence of the recombinant fragment constructed in step (2) is shown in SEQ ID NO.58.

Further, in step (3), the β-1,4-galactotransferase gene, the $P_{43}$ promoter and the bleomycin resistance gene sequence in the recombinant fragment constructed in step (1) are integrated between the ydaH site and the ydzA site of the genome by homologous recombination.

Further, in step (4), the β-1,4-galactotransferase gene, the $P_{43}$ promoter and the chloramphenicol resistance gene sequence in the recombinant fragment constructed in step (2) are integrated between the yszA site and the ysxE site of the genome by homologous recombination.

In a third aspect, the disclosure further provides application of the recombinant *Bacillus subtilis* in fermentation production of lacto-N-neotetraose.

The disclosure has the following beneficial effects:

According to the disclosure, the expression of the β-1,4-galactotransferase is increased by increasing two copy numbers of β-1,4-galactotransferase genes in a genome, thereby increasing the enzyme activity, accelerating precursor transformation, and significantly increasing the yield of lacto-N-neotetraose. The recombinant *Bacillus subtilis* for synthesizing lacto-N-neotetraose according to the disclosure has an extracellular accumulation of 1300 mg/L, which is 80% higher than that of the strain before transformation, laying a foundation for further metabolic engineering transformation of *Bacillus subtilis* for producing the lacto-N-neotetraose. A fermentation method provided by the disclosure for synthesizing the lacto-N-neotetraose is simple in operation, convenient for industrialization, and good in application prospects.

DETAILED DESCRIPTION

Figure 1:
FIG. 1 is a PCR agarose gel electrophoresis diagram of recombinant BY03a strain according to the disclosure.

The disclosure is explained in detail below with reference to the embodiments and the accompanying drawings.

Embodiment 1 Construction of Recombinant PZL($P_{43}$-lacY) Fragment

By using a genome of *Bacillus subtilis* 168 was used as a template, homologous arm primers on both sides were designed according to an amyE gene (Gene ID: 938356) published on NCBI, i.e., the left homologous arm primers of which the sequences are respectively SEQ ID NO:1 and SEQ ID NO:2:

```
amyE-1F:
                                    (SEQ ID NO: 1)
5'-TATTCCGTATGTCAAGTGGCTGCGGTTTAT-3', amyE-1R:
                                    (SEQ ID NO: 2)
5'-AATTGTTATCCGCTCTCTTGACACTCCTTATTTGATTTTTGA

AGACTTACTTCGG-3',
``` and the right homologous arm primers of which the sequences are respectively SEQ ID NO:3 and SEQ ID NO:4:

```
amyE-2F:
                                    (SEQ ID NO: 3)
5'-CTTAAGGGCAAGGCTAGACGGGACTTA-3', amyE-2R:
                                    (SEQ ID NO: 4)
5'-GGCACACCGATGTACACGTCATC-3'.
```

The homologous arm gene sequences on both sides of amyE were amplified from the genome of *Bacillus subtilis* by using the above primers. By using a plasmid pP43NMK as a template, primers of which the sequences are SEQ ID NO:5 and SEQ ID NO:6 were designed respectively:

```
P43-F:
                                    (SEQ ID NO: 5)
5'-CATTATACGAACGGTAAATCTGATAGGTGGTATGTTTTCGCTT

GAACTTTTAAATACAG-3',

P43-R:
                                    (SEQ ID NO: 6)
5'-AGTTTGTGTTTTTTAAATAGTACATGTGTACATTCCTCTCTTA

CCTATAATGGTACCGC-3'.
```

An amplified fragment of $P_{43}$ was obtained by using the above primers. By using a plasmid P7Z6 as a template, bleomycin resistance gene amplified primers of which the sequences are respectively SEQ ID NO:7 and SEQ ID NO:8 were designed:

```
zeo-F:
                                    (SEQ ID NO: 7)
5'-TCAAATAAGGAGTGTCAAGAGAGCGGATAACAATTTCACACAG

GAAACAG-3', zeo-R:
                                    (SEQ ID NO: 8)
5'-AACATACCACCTATCAGATTTACCGTTCGTATAATGTATGCTA

TACGAAGTTATTCAGT-3'.
```

An amplified fragment of the bleomycin resistance gene was obtained by using the above primers. The amplified fragment of the $P_{43}$ and the amplified fragment of the bleomycin resistance gene were verified to be correct by running the gel and then recovered by columns. The amplified fragment of the $P_{43}$ and the amplified fragment of the bleomycin resistance gene were fused by a fusion PCR technology. The conditions of the first round of PCR were: the total amount of $P_{43}$ and bleomycin resistant DNA recovered by equimolar columns was greater than 1000 ng, the amount of primer star enzyme was 25 µL, the volume was adjusted to 50 µL with $ddH_2O$, and the PCR conditions were 55° C., 11 cycles. The conditions of the second round of PCR were: the above PCR product was used as a template, zeo-F and P43-R were used as upstream and downstream primers respectively, and a ZP43 fragment was obtained according to conventional PCR set conditions.

By using a genome of *Escherichia coli* K-12 as a template, primers of which the sequences are respectively SEQ ID NO:9 and SEQ ID NO:10 were designed according to lactose permease gene lacY (Gene ID: 949083) published on NCBI.

```
lacY-F:
                                    (SEQ ID NO: 9)
5'-GTAAGAGAGGAATGTACACATGTACTATTTAAAAAACACAAAC

TTTTGGATGTTCGGTT-3', lacY-R:
                                    (SEQ ID NO: 10)
5'-TAAGTCCCGTCTAGCCTTGCCCTTAAGCGACTTCATTCACCTG

ACGACG-3'.
```

A lactose permease gene fragment was amplified by using the above primers. A left homologous arm of the amyE gene, a right homologous arm of the amyE gene, the ZP43 fragment and the lactose permease gene fragment were verified to be correct by running the gel and then recovered by columns. The left homologous arm of the amyE gene, the right homologous arm of the amyE gene, the ZP43 fragment and the lactose permease gene fragment were fused by a fusion PCR technology. The conditions of the first round of PCR were: the total amount of DNA recovered by equimolar columns was greater than 1000 ng, the amount of primer star enzyme was 25 µL, the volume was adjusted to 50 µL with ddH$_2$O, and the PCR conditions were 55° C., 11 cycles. The conditions of the second round of PCR were: the above PCR product was used as a template, the sequences as shown in SEQ ID NO:11 and SEQ ID NO:12:

zong-F:5'-CATGTAAGCCATAAGCCATTCGTAA-3' (SEQ ID NO:11), zong-R:5'-AGCAAGACTCATCGCAACCC-3' (SEQ ID NO:12) were respectively used as upstream and downstream primers respectively, and a PZL fragment was obtained according to conventional PCR set conditions. The sequence of the recombinant fragment PZL was shown in SEQ ID NO:13.

Embodiment 2 Construction of Recombinant P$_{xylA}$-comk Fragment

By using a genome of Bacillus subtilis 168 as a template, homologous arm primers on both sides were designed, i.e., the left homologous arm primers of which the sequences are respectively SEQ ID NO:14 and SEQ ID NO:15:

```
yhzC-F:
                                        (SEQ ID NO: 14)
5'-CATACATAGGAAGCAGGCATTGTTCATAAC-3', yhzC-R:
                                        (SEQ ID NO: 15)
5'-atacgggatcaaatccgatgaaagagaaaaaatcgtacactga gctc-3',
``` and the right homologous arm primers of which the sequences are respectively SEQ ID NO:16 and SEQ ID NO:17:

```
comK-F:
                                        (SEQ ID NO: 16)
5'-aaggggaaatgggatccatgagtcagaaaacagacgca cct-3', comK-R:
                                        (SEQ ID NO: 17)
5'-ACTACCTCAGTTGAAGGCTATAATCCAAG-3'.
```

The homologous arm gene sequences on both sides were amplified from the genome of the Bacillus subtilis by using the above primers. By using a plasmid pLCx-dcas9 as a template, primers of which the sequences are SEQ ID NO:18 and SEQ ID NO:19 were designed respectively:

```
P$_{xylA}$-F:
                                        (SEQ ID NO: 18)
5'-tttctctttcatcggatttgatcccgtataccgttcgtatagc atacattat-3', P$_{xylA}$-R:
                                        (SEQ ID NO: 19)
5'-gactcatggatcccatttccccctttgattttagatatc ac-3'.
```

An amplified fragment of a P$_{xylA}$ promoter with chloramphenicol resistance was obtained by using the above primers. The recombinant homologous arms and the promoter with the resistance gene were fused by fusion PCR. The conditions of the first round of PCR were: the total amount of DNA recovered by equimolar columns was greater than 1000 ng, the amount of primer star enzyme was 25 µL, the volume was adjusted to 50 µL with ddH$_2$O, and the PCR conditions were 55° C., 11 cycles. The conditions of the second round of PCR were: the above PCR product was used as a template, the sequences as shown in SEQ ID NO:20 and SEQ ID NO:21:

```
zong-F:
                                        (SEQ ID NO: 20)
5'-gacccgcgtccggttttgataagccgaagaaag-3', zong-R:
                                        (SEQ ID NO: 21)
5'-agtaaattcagttgcgcccggaccaatttggacac-3',
``` were respectively used as upstream and downstream primers respectively, and a P$_{xylA}$-comk fragment was obtained according conventional PCR set conditions. The sequence of the fragment P$_{xylA}$-comk was shown in SEQ ID NO:22.

Embodiment 3 Construction of p7S6P43-lgtB Fragment

By using a genome of Bacillus subtilis 168 as a template, homologous arm primers on both sides were designed, i.e., the left homologous arm primers of which the sequences are respectively SEQ ID NO:23 and SEQ ID NO:24:

```
ydeS-F:
                                        (SEQ ID NO: 23)
5'-gggacaaggaatagtaagccggcaa-3', ydeS-R:
                                        (SEQ ID NO: 24)
5'-tcctgtgtgaaattgttatccgctcctacatactctctgtagcagagg tagcttga',
``` and the right homologous arm primers of which the sequences are respectively SEQ ID NO:25 and SEQ ID NO:26:

```
ydzO-F:
                                        (SEQ ID NO: 25)
5'-tgaagcccgcctaatgagcgggctttttctgataagaactgcaaaag ctgcggattat-3', ydzO-R:
                                        (SEQ ID NO: 26)
5'-ccaccctatagataaattttcggctgccatat-3'.
```

The homologous arm gene sequences on both sides were amplified from the genome of Bacillus subtilis by using the above primers.

By using a plasmid p7S6P43 as a template, primers of which the sequences are SEQ ID NO:27 and SEQ ID NO:28 were designed respectively:

```
p7S6P43-F:
                                        (SEQ ID NO: 27)
5'-agagtatgtaggagcggataacaatttcacacagga-3', p7S6P43-R:
                                        (SEQ ID NO: 28)
5'-AAAGAAATGACATGATTTTGCATgtgtacattcctctcttacctataa tggtaccgc-3'.
```

By using a plasmid pP43NMK-lgtA-lgtB as a template, primers of which the sequences are SEQ ID NO:29 and SEQ ID NO:30 were designed respectively (disclosed in patent CN108410787A):

IgtB-F:
(SEQ ID NO: 29)
5'-aggtaagagaggaatgtacacATGCAAAATCATGTCATTTCTTTAGCA

TCAGCAG-3',

IgtB-R:
(SEQ ID NO: 30)
5'-cccgctcattaggcgggcttcatcaTTACTGAAACGGAACGATAAACT

GTTCGCG-3'.

By using the above primers, the obtained amplified fragments were verified to be correct by running the gel and then recovered by columns. Recombinant homologous arms, a β-1,4-galactotransferase encoding gene and a promoter with the resistance gene were fused by fusion PCR. The conditions of the first round of PCR were: the total amount of DNA recovered by equimolar columns was greater than 1000 ng, the amount of primer star enzyme was 25 μL, the volume was adjusted to 50 μL with ddH$_2$O, and the PCR conditions were 55° C., 11 cycles. The conditions of the second round of PCR were: the above PCR product was used as a template, the sequences as shown in SEQ ID NO:31 and SEQ ID NO:32:

zong-F:5'-CGTATCCGATTTGGGTGAGTGTGA-3' (SEQ ID NO:31), zong-R:5'-TGATGTCAATCTAATGCCTCCTTACTGG-3' (SEQ ID NO:32) were respectively used as upstream and downstream primers respectively, and a p7S6P43-lgtB fragment was obtained according to conventional PCR set conditions. The sequence of the p7S6P43-lgtB fragment was shown in SEQ ID NO:33.

Embodiment 4 Construction of Recombinant Plasmid pP43NMK-lgtA

By using a recombinant plasmid pP43NMK-lgtA-lgtB as a template, reverse recombinant primers were designed. The sequences of the reverse recombinant primers were respectively SEQ ID NO:34 and SEQ ID NO:35:

fz-IgtA-F:
(SEQ ID NO: 34)
5'-tgaagcccgcctaatgagcgggcttttttaagcttggcgtaatcatgg tcatagctgtt-3', fz-IgtA-R:
(SEQ ID NO: 35)
5'-CTGTGTGAAATTGTTATCCGCTCCCAGCCTTTCTTATTAAAACCACTT

TGTCAGCC-3'.

After using the above primers to verify that the obtained amplified fragment is correct by running the gel, 10 μL of PCR reaction system was taken to transform an *Escherichia coli* JM109 competent cell. By sequencing, it was verified that the recombinant plasmid pP43NMK-lgtA was successfully constructed, and the gene sequence of the recombinant plasmid pP43NMK-lgtA was shown in SEQ ID NO:36.

Embodiment 5 Construction of Recombinant p7Z6P43-lgtB Fragment

By using a genome of *Bacillus subtilis* 168 as a template, homologous arm primers on both sides were designed, i.e., the left homologous arm primers of which the sequences are respectively SEQ ID NO:37 and SEQ ID NO:38:

ydaH-F:
(SEQ ID NO: 37)
5'-GGCTTTCGTTGTCTTGTGTTCAAGAAATTTCCA-3', ydaH-R:
(SEQ ID NO: 38)
5'-CTGTGTGAAATTGTTATCCGCTCCCAGCCTTTCTTATTAAACCACTT

TGTCAGCC-3', and the right homologous arm primers of which the sequences are respectively SEQ ID NO:39 and SEQ ID NO:40:

ydZA-F:
(SEQ ID NO: 39)
5'-AAGCCCGCCTAATGAGCGGGCTTTTTTATCATAAAGATCCAGCCTTTT

TGCGCT-3', ydZA-R:
(SEQ ID NO: 40)
5'-CTAAAGCCCAAGTCACAATATATTGATCGCCT-3'.

By using a plasmid p7Z6P43 as a template, primers of which the sequences are SEQ ID NO:41 and SEQ ID NO:42 were designed respectively:

p7Z6P43-F:
(SEQ ID NO: 41)
5'-GTTTTAATAAGAAAGGCTGGGAGCGGATAACAATTTCACACAGGAAAC

AGC-3', p7Z6P43-R:
(SEQ ID NO: 42)
5'-AAAGAAATGACATGATTTTGCATGTGTACATTCCTCTCTTACCTATAA

TGGTACCGC-3'.

By using a genome of the starting strain *Bacillus subtilis* 168ΔamyE:P$_{43}$-lacY, P$_{43}$-lgtB, P$_{xylA}$-comK as a template, primers of which the sequences are SEQ ID NO:43 and SEQ ID NO:44 were respectively designed:

IgtB-1F:
(SEQ ID NO: 43)
5'-AGGTAAGAGAGGAATGTACACATGCAAAATCATGTCATTTCTTTAGCA

TCAGCAG-3',

IgtB-1R:
(SEQ ID NO: 44)
5'-CCCGCTCATTAGGCGGGCTTCATCATTACTGAAACGGAACGATAAACT

GTTCGCG-3'.

By using the above primers, the obtained amplified fragments were verified to be correct by running the gel and then recovered by columns. Recombinant homologous arms, a β-1,4-galactotransferase encoding gene and a promoter with the resistance gene were fused by fusion PCR. The conditions of the first round of PCR were: the total amount of DNA recovered by equimolar columns was greater than 1000 ng, the amount of primer star enzyme was 25 μL, the volume was adjusted to 50 μL with ddH$_2$O, and the PCR conditions were 55° C., 11 cycles. The conditions of the second round of PCR were: the above PCR product was used as a template, primers for fusion PCR were respectively SEQ ID NO:45 and SEQ ID NO:46:

zong-1F:5'-AACCTCCTTGTCTTCTTTCCAGTCT-TATCTC-3' (SEQ ID NO:45), zong-1R:5'-ATCACTTCTCTTTCTTTCACGCT-CATCCT-3' (SEQ ID NO:46), and a p7Z6P43-lgtB fragment was obtained according to the set conditions of conventional PCR. The sequence of the p7Z6P43-lgtB fragment was shown in SEQ ID NO:47.

Embodiment 6 Construction of Recombinant p7C6P43-lgtB Fragment

By using a genome of *Bacillus subtilis* 168 as a template, homologous arm primers on both sides were designed, i.e., the left homologous arm primers of which the sequences are respectively SEQ ID NO:48 and SEQ ID NO:49:

yszA-F:
(SEQ ID NO: 48)
5'-CATCCAGCGTAAAACGTTCACGGGAATAATCTAGG-3', yszA-R:
(SEQ ID NO: 49)
5'-TTATCCGCTCTGGCGCGGACTTGTTTGTTTATATCCATTCTAAATGAA

GG-3', and the right homologous arm primers of which the sequences are respectively SEQ ID NO:50 and SEQ ID NO:51:

ysxE-F:
(SEQ ID NO: 50)
5'-GCCCGCCTAATGAGCGGGCTTTTTTTTAAGACGTGGACTCGTTTTCAG

CCTGAAATTTT-3', ysxE-R:
(SEQ ID NO: 51)
5'-CATCCCAGCAGCTGATCAGGATGAATTCT-3'.

By using a plasmid p7C6P43 as a template, primers of which the sequences are SEQ ID NO:52 and SEQ ID NO:53 were designed respectively:

p7C6P43-F:
(SEQ ID NO: 52)
5'-ACAAGTCCGCGCCAGAGCGGATAACAATTTCACACAGGAAACAGCTAT

G-3', p7C6P43-R:
(SEQ ID NO: 53)
5'-AGAAATGACATGATTTTGCATGTGTACATTCCTCTCTTACCTATAATG

GTACCGCT-3'.

By using the genome of the starting strain as a template, primers of which the sequences are SEQ ID NO:54 and SEQ ID NO:55 were designed respectively:

IgtB-2F:
(SEQ ID NO: 54)
5'-ATAGGTAAGAGAGGAATGTACACATGCAAAATCATGTCATTTCTTTAG

CATCAGCAGCG-3',

IgtB-2R:
(SEQ ID NO: 55)
5'-GCCCGCTCATTAGGCGGGCTTCATCATTACTGAAACGGAACGATAAAC

TGTTCGCGT-3'.

By using the above primers, the obtained amplified fragments were verified to be correct by running the gel and then recovered by columns. Recombinant homologous arms, a β-1,4-galactotransferase encoding gene and a promoter with the resistance gene were fused by fusion PCR. The conditions of the first round of PCR were: the total amount of DNA recovered by equimolar columns was greater than 1000 ng, the amount of primer star enzyme was 25 μL, the volume was adjusted to 50 μL with ddH$_2$O, and the PCR conditions were 55° C., 11 cycles. The conditions of the second round of PCR were: the above PCR product was used as a template, primers for fusion PCR were respectively SEQ ID NO:56 and SEQ ID NO:57:

zong-2F:
(SEQ ID NO: 56)
5'-GCCAGGAAGCCACAGCACATCATAGC-3', zong-2R:
(SEQ ID NO: 57)
5'-TTCGTTCATTCGTTCCCGTTTACAGAACAAATAGC-3', and a p7C6P43-lgtB fragment was obtained according to conventional PCR set conditions. The sequence of the p7C6P43-lgtB fragment was shown in SEQ ID NO:58.

Embodiment 7 Construction of Starting Strain *Bacillus subtilis*

A constructed recombinant fragment PxylA-comK was transformed into *Bacillus subtilis* competent cells (*Bacillus subtilis* 168). The addition amount of the recombinant fragment is 100-300 ng. The conditions for electrotransformation were: the voltage was 2.5 kV, the electroshock reagent was 5 ms, after performing recovery at 37° C. for 5 h, a chloramphenicol-resistant plate was coated, and culture was carried out at 37° C. for 24 h to obtain recombinant *Bacillus subtilis* BS168comk.

Competent cells were prepared from BS168comk recombinant *Bacillus subtilis* by xylose induction. After performing culture in an LB liquid medium at 37° C. and 220 rpm for 12 h, the OD600 was diluted to 1 with the LB liquid medium, xylose with a final concentration of 2% was added, and culture was continued to be carried out for 2 h to obtain the BS168comk competent cells. The addition amount of a recombinant fragment PZL is 500 ng. The cells were cultured at 37° C. for 1 h, and a bleomycin resistant plate was coated with the cells and cultured over night at 37° C. to obtain recombinant *Bacillus subtilis* BY00.

Competent cells were prepared from The BY00 by xylose induction. The addition amount of a recombinant fragment p7S6P43-lgtB was 500 ng. After performing culture at 37° C. for 1 h, a spectinomycin resistant plate was coated, and culture was carried out at 37° C. overnight to obtain recombinant *Bacillus subtilis* BY01. A resistance gene was knocked out by a Cre/lox recombination system to obtain BY01.2 bacteria.

Competent cells were prepared from the BY01.2 by xylose induction. The addition amount of the recombinant plasmid pP43NMK-lgtA was 500 ng. After performing culture at 37° C. for 1 h, a kanamycin resistant plate was coated, and culture was carried out at 37° C. overnight to obtain a strain BY03.

Embodiment 8

A constructed recombinant p7Z6P43-lgtB fragment was transformed into competent cells BY01.2. Transformants were selected for colony PCR verification, and primers for verification of primer sequences SEQ ID NO:59 and SEQ ID NO:60 were designed respectively:
YZ-1F:5'-CGAAGGAATGCCGGTGTGCCAACT-GAATC-3' (SEQ ID NO:59),
YZ-1R:5'-CGACCTCCAGCGTGTATTGCTTGAT-GATGC-3' (SEQ ID NO:60), and recombinant *Bacillus subtilis* BY03a was obtained after verifying the primer sequences to be correct. The colony PCR agarose gel electrophoresis diagram is shown in FIG. 1.

A recombinant plasmid pP43NMK-lgtA was transformed into the recombinant *Bacillus subtilis* BY03a. After performing culture at 37° C. for 1 h, a kanamycin resistant plate was coated, and culture was carried out at 37° C. overnight to obtain recombinant *Bacillus subtilis* BY04.

A constructed recombinant p7C6P43-lgtB fragment was transformed into the recombinant *Bacillus subtilis* BY03a competent cells. Transformants were selected for colony PCR verification, and primers for verification of primer sequences SEQ ID NO:61 and SEQ ID NO:62 were designed respectively:

```
YZ-2F:
                                    (SEQ ID NO: 61)
5'-GGGCACAGCGGGATACATCATCTCAAGAAA-3',

YZ-2R:
                                    (SEQ ID NO: 62)
5'-TGAACCACGGCAGCCTGTCTATACACCAT-3'.
```

Figure 2:
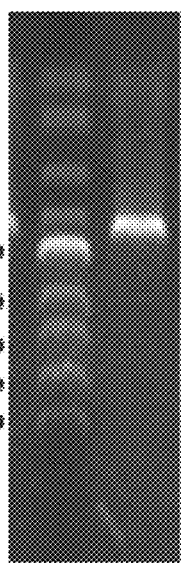
FIG. 2 is a PCR agarose gel electrophoresis diagram of the recombinant BY03b strain according to the disclosure.

Recombinant *Bacillus subtilis* BY03b was obtained after verifying the primer sequences to be correct, and the obtained colony PCR agarose gel electrophoresis diagram is shown in FIG. 2.

A recombinant plasmid pP43NMK-lgtA was transformed into the recombinant *Bacillus subtilis* BY03b. After performing culture at 37° C. for 1 h, a kanamycin resistant plate was coated, and culture was carried out at 37° C. overnight to obtain recombinant *Bacillus subtilis* BY05 for synthesizing lacto-N-neotetraose.

Plasmids pLCx-dcas9, p7S6P43, p7Z6P43 and p7C6P43 used were from the Institute of Biological Engineering, Lab of Biosystem and Bioprocessing Engineering, No. 1800, Lihu Avenue, Binhu District, Wuxi, Jiangsu Province. The plasmids p7S6P43, p7Z6P43 and p7C6P43 have been disclosed in Modular pathway engineering of key carbon-precursor supply-pathways for improved N-acetylnuraminic acid production in *Bacillus subtilis* (Zhang X L, Liu Y F, Liu L, Wang M, Li J H, Du G C, Chen J. 2018). The plasmid pLCx-dcas9 has been disclosed in CRISPRi allows optimal temporal control of Nacetylglucosamine bioproduction by a dynamic coordination of glucose and xylose metabolism in *Bacillus subtilis* (Wu Y K, Chen T C, Liu Y F, Lv X Q, Li J H, Du G C, Amaro R L, Liu L. 2018).

Embodiment 9 Production of Lacto-N-Neotetraose from Recombinant *Bacillus subtilis* by Fermentation The recombinant *Bacillus subtilis* BY05 in Embodiment 8 was prepared into a seed solution. A preparation method of the seed solution was: a single colony on the plate was selected and placed in a seed culture medium (the seed culture medium contains tryptone 10 g/L, yeast powder 5 g/L, and NaCl 10 g/L). Meanwhile, kanamycin with a final concentration of 30 μg/mL was added, and culture was carried out at 37° C. and 220 rpm for 10-12 h.

The seed solution was transferred into a fermentation medium according to an inoculation amount of 10% (the fermentation medium contains tryptone 6 g/L, yeast powder 12 g/L, $(NH_4)SO_4$ 6 g/L, $K_2HPO_4 \cdot 3H_2O$ 12.5 g/L, $KH_2PO_4$ 2.5 g/L, $MgSO_4 \cdot 7H_2O$ 1.2 g/L, glucose 60 g/L, and lactose 5 g/L), and culture was carried out at 37° C. and 220 rpm for 48 h. Lacto-N-neotetraose was detected in the supernatant of a fermentation broth, and the content was 1300 mg/L. The yield was improved by 80.6% compared with the strain (*Bacillus subtilis* 168ΔamyE:$P_{43}$-lacY, $P_{43}$-lgtB, PxylA-comK, pP43NMK-lgtA), efficient synthesis of lacto-N-neotetraose from recombinant *Bacillus subtilis* was realized, and a foundation was laid for further metabolic engineering transformation of *Bacillus subtilis* to produce lacto-N-neotetraose and complicated oligosaccharides with the lacto-N-neotetraose as a core element.

Comparative Embodiment 1 Production of Lacto-N-Neotetraose from BY03 and BY04 Strains by Fermentation

*Bacillus subtilis* 168ΔamyE:$P_{43}$-lacY, $P_{43}$-lgtB, $P_{xylA}$-comK, pP43NMK-lgtA and recombinant *Bacillus subtilis* BY04 were prepared into a seed solution. The preparation method of the seed solution was: a single colony on the plate was selected and placed in a seed culture medium. Meanwhile, kanamycin with a final concentration of 30 μg/mL was added, and culture was carried out at 37° C. and 220 rpm for 10-12 h.

Figure 3:
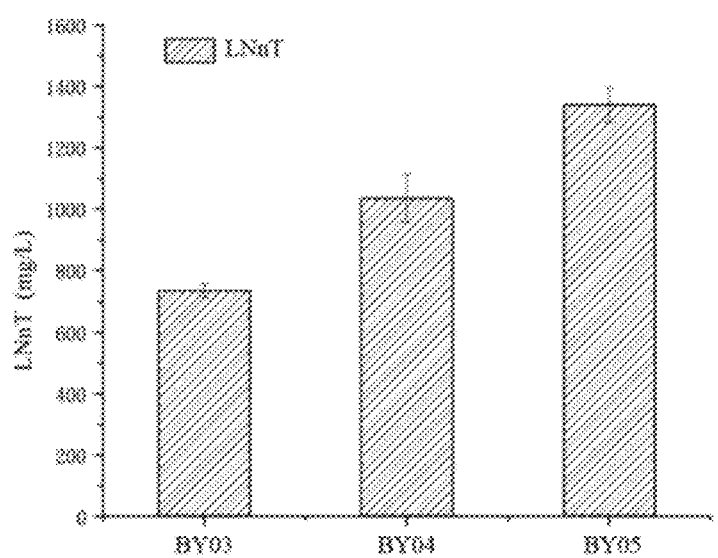
FIG. 3 shows the effect of increasing the copy number of lgtB genes on the yield of lacto-N-neotetraose according to the disclosure.

The seed solution was transferred into a fermentation medium according to an inoculation amount of 10% and culture was carried out at 37° C. and 220 rpm for 48 h. Lacto-N-neotetraose was detected in the supernatant of a fermentation broth, the content of BY03 in the supernatant was about 720 mg/L, and the content of the recombinant *Bacillus subtilis* BY04 in the supernatant was about 1090 mg/L. The yield of recombinant *Bacillus subtilis* BY04 was 51.3% higher than that of the starting strain (*Bacillus subtilis* 168ΔamyE:$P_{43}$-lacY, P43-lgtB, $P_{xylA}$-comK, pP43NMK-lgtA), and was 16% lower than the yield of lacto-N-neotetraose in BY05 which was 1300 mg/L, as shown in FIG. 3. It is known that a genome of BY05 bacteria has 2 copy numbers of β-1,4-galactotransferase encoding genes, and the genome of the BY05 bacteria having 3 copy numbers of β-1,4-galactotransferase encoding genes indicates that increasing the copy number of key genes effectively improves the synthesis efficiency of lacto-N-neotetraose from recombinant *Bacillus subtilis*.

Although the disclosure has been disclosed above with the preferred embodiments, it is not intended to limit the disclosure. Any person skilled in the art can make various changes and modifications without departing from the spirit and scope of the disclosure. Therefore, the scope of the disclosure should be determined by the scope of the claims.

What is claimed is:

1. A recombinant *Bacillus subtilis* obtained by integrating two β-1,4-galactotransferase genes on a genome of a host bacterium *Bacillus subtilis* 168ΔamyE:P$_{43}$-lacY, P$_{43}$-lgtB, P$_{xylA}$-comK; and exogenously expressing a β-1,3-N-glucose aminotransferase gene.

2. The recombinant *Bacillus subtilis* obtained by the process of claim 1, wherein the host bacterium is *Bacillus subtilis* 168, and further comprising:
   regulating the expression of a gene comK by a promoter P$_{xylA}$;
   integrating a lactose permease-encoding gene onto an amyE site of the genome, and
   integrating a β-1,4-galactotransferase-encoding gene between a ydeS site and a ydzO site of the genome.

3. A method for constructing the recombinant *Bacillus subtilis* of claim 1, which comprises:
   (a) constructing a recombinant fragment containing homologous arms of ydaH and ydzA genes, a β-1,4-galactotransferase gene, a P$_{43}$ promoter, and a bleomycin resistance gene sequence by fusion PCR;
   (b) constructing a recombinant fragment containing homologous arms of yszA and ysxE genes, a β-1,4-galactotransferase gene, a P$_{43}$ promoter, and a chloramphenicol resistance gene sequence by fusion PCR;
   (c) transforming the recombinant fragment constructed in the step (a) into *Bacillus subtilis* 168ΔamyE:P$_{43}$-lacY, P$_{43}$-lgtB, PxylA-comK, and verifying to obtain recombinant *Bacillus subtilis* BY03a;
   (d) transforming the recombinant fragment constructed in the step (b) into the recombinant *Bacillus subtilis* BY03a of the step (c), and verifying to obtain recombinant *Bacillus subtilis* BY03b; and
   (e) transforming pP43NMK-lgtA into the recombinant *Bacillus subtilis* BY03b to obtain recombinant *Bacillus subtilis* BY05.

4. The method of claim 3, wherein in the step (a), the homologous arms of ydaH and ydzA genes comprise a left homologous arm of a ydaH gene and a right homologous arm of a ydzA gene.

5. The method of claim 3, wherein in the step (b), the homologous arms of ydaH and ydzA genes comprise a left homologous arm of a yszA gene and a right homologous arm of a ysxE gene.

6. The method of claim 3, wherein a sequence of the recombinant fragment constructed in the step (a) is set forth in SEQ ID NO:47, and a sequence of the recombinant fragment constructed in the step (b) is set forth in SEQ ID NO:58.

7. The method of claim 3, wherein in the step (c), the β-1,4-galactotransferase gene, the P$_{43}$ promoter, and the bleomycin resistance gene sequence in the recombinant fragment constructed in the step (a) are integrated between a ydaH site and a ydzA site of the genome by homologous recombination.

8. The method of claim 3, wherein in the step (d), the β-1,4-galactotransferase gene, the P$_{43}$ promoter, and the chloramphenicol resistance gene sequence in the recombinant fragment constructed in the step (b) are integrated between a yszA site and a ysxE site of the genome by homologous recombination.

9. A method for producing lacto-N-neotetraose, comprising incubating the recombinant *Bacillus subtilis* of claim 2 under conditions that cause fermentation at 35° C. to 40° C.

10. The method of claim 9, wherein the recombinant *Bacillus subtilis* is fermented in a culture medium comprising glucose and lactose.

11. The method of claim 10, wherein the culture medium comprises:
   6 g/L tryptone,
   12 g/L yeast powder,
   6 g/L (NH$_4$)SO$_4$,
   12.5 g/L K$_2$HPO$_4$·3H$_2$O,
   2.5 g/L KH$_2$PO$_4$,
   1.2 g/L MgSO$_4$·7H$_2$O,
   60 g/L glucose, and
   5 g/L lactose.

12. The method of claim 10, wherein fermenting comprises inoculating the culture medium with 10% by volume of a recombinant *Bacillus subtilis* seed solution, and wherein the seed solution is obtained by culturing the recombinant *Bacillus subtilis* in a seed culture medium at 35° C. to 37° C. for 10 hours to 12 hours.

13. The method of claim 12, wherein the seed culture medium is an Luria Broth culture medium comprising 10 g/L tryptone, 5 g/L yeast powder, and 10 g/L NaCl.

* * * * *

SEQUENCE LISTING

<160> NUMBER OF SEQ ID NOS: 62

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
tattccgtat gtcaagtggc tgcggtttat                                          30

<210> SEQ ID NO 2
<211> LENGTH: 56
<212> TYPE: DNA
<213> ORGANISM: Artificial Sequence
<220> FEATURE:
<223> OTHER INFORMATION: Synthetic DNA

<400> SEQUENCE: 2
aattgttatc cgctctcttg acactcctta tttgattttt tgaagactta cttcgg            56

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
cttaagggca aggctagacg ggactta                                             27

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA

<400> SEQUENCE: 4
ggcacaccga tgtacacgtc atc                                                 23

<210> SEQ ID NO 5
<211> LENGTH: 59
<212> TYPE: DNA
<213> ORGANISM: Artificial Sequence
<220> FEATURE:
<223> OTHER INFORMATION: Synthetic DNA

<400> SEQUENCE: 5
cattatacga acggtaaatc tgataggtgg tatgttttcg cttgaacttt taaatacag          59

<210> SEQ ID NO 6
<211> LENGTH: 59
<212> TYPE: DNA
<213> ORGANISM: Artificial Sequence
<220> FEATURE:
<223> OTHER INFORMATION: Synthetic DNA

<400> SEQUENCE: 6
agtttgtgtt ttttaaatag tacatgtgta cattcctctc ttacctataa tggtaccgc          59

<210> SEQ ID NO 7
<211> LENGTH: 50
<212> TYPE: DNA
<213> ORGANISM: Artificial Sequence

```
<220> FEATURE:
<223> OTHER INFORMATION: Synthetic DNA

<400> SEQUENCE: 7
tcaaataagg agtgtcaaga gagcggataa caatttcaca caggaaacag        50

<210> SEQ ID NO 8
<211> LENGTH: 59
<212> TYPE: DNA
<213> ORGANISM: Artificial Sequence
<220> FEATURE:
<223> OTHER INFORMATION: Synthetic DNA

<400> SEQUENCE: 8
aacataccac ctatcagatt taccgttcgt ataatgtatg ctatacgaag ttattcagt   59

<210> SEQ ID NO 9
<211> LENGTH: 59
<212> TYPE: DNA
<213> ORGANISM: Artificial Sequence
<220> FEATURE:
<223> OTHER INFORMATION: Synthetic DNA

<400> SEQUENCE: 9
gtaagagagg aatgtacaca tgtactattt aaaaaacaca aactttkgga tgttcggtt   59

<210> SEQ ID NO 10
<211> LENGTH: 49
<212> TYPE: DNA
<213> ORGANISM: Artificial Sequence
<220> FEATURE:
<223> OTHER INFORMATION: Synthetic DNA

<400> SEQUENCE: 10
taagtcccgt ctagccttgc ccttaagcga cttcattcac ctgacgacg         49

<210> SEQ ID NO 11
<211> LENGTH: 25
<212> TYPE: DNA
<213> ORGANISM: Artificial Sequence
<220> FEATURE:
<223> OTHER INFORMATION: Synthetic DNA

<400> SEQUENCE: 11
catgtaagcc ataagccatt cgtaa                       25

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
agcaagactc atcgcaaccc                           20

<210> SEQ ID NO 13
<211> LENGTH: 3811
<212> TYPE: DNA
<213> ORGANISM: Artificial Sequence
<220> FEATURE:
<223> OTHER INFORMATION: Synthetic DNA

<400> SEQUENCE: 13
catgtaagcc ataagccatt cgtaaaagtg cgggaggaag gtcatgaata atctgcgtaa   60
```

-continued

```
tagactttca ggcgtgaatg ggaaaaataa gagagtaaaa gaaaaagaac aaaaaatctg      120
gtcggagatt gggatgatag cgggagcatt tgcgctgctt gatgtgatca tccgcggcat      180
tatgtttgaa tttccgttta agaatgggc tgcaagcctt gtgttttgt tcatcattat        240 cttatattac tgcatcaggg ctgcggcatc cggaatgctc atgccgagaa tagacaccaa      300
agaagaactg caaaaacggg tgaagcagca gcgaatagaa tcaattgcgg tcgcctttgc     360
ggtagtggtg cttacgatgt acgacagggg gattccccat acattcttcg cttggctgaa     420
aatgattctt cttttatcg tctgcggcgg cgttctgttt ctgcttcggt atgtgattgt       480
gaagctggct tacagaagag cggtaaaaga agaaataaaa aagaaatcat cttttttgtt     540
tggaaagcga gggaagcgtt cacagtttcg ggcagctttt tttataggaa cattgatttg     600
tattcactct gccaagttgt tttgatagag tgattgtgat aattttaaat gtaagcgtta     660
acaaaattct ccagtcttca catcggtttg aaaggaggaa gcggaagaat gaagtaagag    720 ggattttga ctccgaagta agtcttcaaa aaatcaaata aggagtgtca agagagcgga      780
taacaatttc acacaggaaa cagctatgac catgattacg aattcgagct cggtacccgg     840
ggatcctcta gagataccgt tcgtatagca tacattatac gaagttatct tgatatggct     900
ttttatatgt gttactctac atacagaaag gaggaactaa acatggccaa gttgaccagt    960
gccgttccgg tgctcaccgc gcgcgacgtc gccggagcgg tcgagttctg gaccgaccgg    1020
ctcgggttct cccgggactt cgtggaggac gacttcgccg gtgtggtccg ggacgacgtg    1080
accctgttca tcagcgcggt ccaggaccag gtggtgccgg acaacaccct ggcctgggtg    1140
tgggtgcgcg gcctggacga gctgtacgcc gagtggtcgg aggtcgtgtc cacgaacttc    1200
cgggacgcct ccgggccggc catgaccgag atcggcgagc agccgtgggg gcgggagttc    1260
gccctgcgcg acccggccgg caactgcgtg cacttcgtgg ccgaggagca ggactgaata    1320
acttcgtata gcatacatta tacgaacggt aaatctgata ggtggtatgt tttcgcttga    1380 actttaaat acagccattg aacatacggt tgatttaata actgacaaac atcaccctct     1440
tgctaaagcg gccaaggacg ccgccgccgg ggctgtttgc gttcttgccg tgatttcgtg    1500
taccattggt ttacttattt ttttgccaag gctgtaatgg ctgaaaattc ttacatttat    1560
tttacatttt tagaaatggg cgtgaaaaaa agcgcgcgat tatgtaaaat ataaagtgat    1620
agcggtacca ttataggtaa gagaggaatg tacacatgta ctatttaaaa aacacaaact    1680
tttggatgtt cggtttattc ttttttcttt acttttttat catgggagcc tacttcccgt    1740
ttttcccgat ttggctacat gacatcaacc atatcagcaa aagtgatacg ggtattattt    1800
ttgccgctat ttctctgttc tcgctattat tccaaccgct gtttggtctg ctttctgaca    1860
aactcgggct cgcaaatac ctgctgtgga ttattaccgg catgttagtg atgtttgcgc     1920
cgttctttat tttatcttc gggccactgt tacaatacaa catttagta ggatcgattg       1980 ttggtggtat ttatctaggc ttttgtttta acgccggtgc gccagcagta gaggcattta    2040
ttgagaaagt cagccgtcgc agtaatttcg aatttggtcg cgcgcggatg tttggctgtg    2100
ttggctgggc gctgtgtgcc tcgattgtcg gcatcatgtt caccatcaat aatcagtttg    2160
ttttctggct gggctctggc tgtgcactca tcctcgccgt tttactcttt ttcgccaaaa    2220
cggatgcgcc ctcttctgcc acggttgcca atgcggtagg tgccaaccat tcggcattta    2280
gccttaagct ggcactggaa ctgttcagac agccaaaact gtggttttg tcactgtatg     2340 ttattggcgt ttcctgcacc tacgatgttt ttgaccaaca gtttgctaat ttctttactt    2400
cgttctttgc taccggtgaa cagggtacgc gggtatttgg ctacgtaacg acaatgggcg    2460
```

```
aattacttaa cgcctcgatt atgttctttg cgccactgat cattaatcgc atcggtggga    2520
aaaacgccct gctgctggct ggcactatta tgtctgtacg tattattggc tcatcgttcg    2580
ccacctcagc gctggaagtg gttattctga aaacgctgca tatgtttgaa gtaccgttcc    2640
tgctggtggg ctgctttaaa tatattacca gccagtttga agtgcgtttt tcagcgacga    2700
tttatctggt ctgtttctgc ttctttaagc aactggcgat gattttatg tctgtactgg     2760 cgggcaatat gtatgaaagc atcggtttcc agggcgctta tctggtgctg ggtctggtgg    2820
cgctgggctt caccttaatt tccgtgttca cgcttagcgg ccccggcccg ctttccctgc    2880
tgcgtcgtca ggtgaatgaa gtcgcttaag ggcaaggcta gacgggactt accgaaagaa    2940
accatcaatg atggtttctt ttttgttcat aaatcagaca aaactttttct cttgcaaaag   3000 tttgtgaagt gttgcacaat ataaatgtga aatacttcac aaacaaaaag acatcaaaga    3060
gaaacatacc ctggaaggat gattaatgat gaacaaacat gtaaataaag tagctttaat    3120
cggagcgggt tttgttggaa gcagttatgc atttgcgtta attaaccaag gaatcacaga    3180
tgagcttgtg gtcattgatg taaataaaga aaaagcaatg ggcgatgtga tggatttaaa    3240
ccacggaaag gcgtttgcgc cacaaccggt caaaacatct tacggaacat atgaagactg    3300
caaggatgct gatattgtct gcatttgcgc cggagcaaac caaaaacctg gtgagacacg    3360
ccttgaatta gtagaaaaga acttgaagat tttcaaaggc atcgttagtg aagtcatggc    3420
gagcggattt gacggcattt tcttagtcgc gacaaatccg gttgatatcc tgacttacgc    3480
aacatggaaa ttcagcggcc tgccaaaaga gcgggtgatt ggaagcggca acacttga     3540 ttctgcgaga ttccgtttca tgctgagcga atactttggc gcagcgcctc aaaacgtaca    3600
cgcgcatatt atcggagagc acggcgacac agagcttcct gttttggagcc acgcgaatgt   3660 cggcggtgtg ccggtcagtg aactcgttga gaaaaacgat gcgtacaaac aagaggagct    3720
ggaccaaatt gtagatgatg tgaaaaacgc agcttaccat atcattgaga aaaaggcgc     3780 gacttattat ggggttgcga tgagtcttgc t                                   3811
```

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14

```
catacatagg aagcaggcat tgttcataac                                      30
```

<210> SEQ ID NO 15
<211> LENGTH: 47
<212> TYPE: DNA
<213> ORGANISM: Artificial Sequence
<220> FEATURE:
<223> OTHER INFORMATION: Synthetic DNA

<400> SEQUENCE: 15

```
atacgggatc aaatccgatg aaagagaaaa aatcgtacac tgagctc                   47
```

<210> SEQ ID NO 16
<211> LENGTH: 42
<212> TYPE: DNA
<213> ORGANISM: Artificial Sequence
<220> FEATURE:
<223> OTHER INFORMATION: Synthetic DNA

<400> SEQUENCE: 16 aaggggaaa tgggatccat gagtcagaaa acagacgcac ct                        42

<210> SEQ ID NO 17
<211> LENGTH: 29
<212> TYPE: DNA
<213> ORGANISM: Artificial Sequence
<220> FEATURE:
<223> OTHER INFORMATION: Synthetic DNA

<400> SEQUENCE: 17
actacctcag ttgaaggcta taatccaag                                      29

<210> SEQ ID NO 18
<211> LENGTH: 52
<212> TYPE: DNA
<213> ORGANISM: Artificial Sequence
<220> FEATURE:
<223> OTHER INFORMATION: Synthetic DNA

<400> SEQUENCE: 18
tttctctttc atcggatttg atcccgtata ccgttcgtat agcatacatt at            52

<210> SEQ ID NO 19
<211> LENGTH: 42
<212> TYPE: DNA
<213> ORGANISM: Artificial Sequence
<220> FEATURE:
<223> OTHER INFORMATION: Synthetic DNA

<400> SEQUENCE: 19
gactcatgga tcccatttcc ccctttgatt tttagatatc ac                       42

<210> SEQ ID NO 20
<211> LENGTH: 34
<212> TYPE: DNA
<213> ORGANISM: Artificial Sequence
<220> FEATURE:
<223> OTHER INFORMATION: Synthetic DNA

<400> SEQUENCE: 20
gacccgcgtc cggttttga taagccgaag aaag                                 34

<210> SEQ ID NO 21
<211> LENGTH: 35
<212> TYPE: DNA
<213> ORGANISM: Artificial Sequence
<220> FEATURE:
<223> OTHER INFORMATION: Synthetic DNA

<400> SEQUENCE: 21
agtaaattca gttgcgcccg gaccaatttg gacac                               35

<210> SEQ ID NO 22
<211> LENGTH: 4568
<212> TYPE: DNA
<213> ORGANISM: Artificial Sequence
<220> FEATURE:
<223> OTHER INFORMATION: Synthetic DNA

<400> SEQUENCE: 22
gacccgcgtc cggttttga taagccgaag aaagcgaaaa aattagaggg caaaaccgct     60
attattactg gaggagacag cgggattgga cgcgctgtct cggtgttatt cgcaaaagaa    120
ggggctaatg tggtcattgt gtatttgaat gaacatcagg acgccgagga aacaaagcag    180

```
tatgtagaaa aggaaggggt aaaatgcctg ctgattgcag gagatgtcgg ggatgaagcg    240
ttttgcaatg atgtggtcgg gcaggcaagc caagtgtttc catccattga tatattggtt    300
aacaatgcag ctgagcagca tgtccagccc agcattgaaa aaatcaccag ccaccagctg    360
atcagaacct tccaaacaaa catttttttcc atgttttact aacaaaggc agtgctgcct    420 catttaaaaa aagggagctc tattattaat accgcttcaa ttaccgccta taaaggcaat    480
aaaacgctga tcgattattc agcgacaaaa ggcgcgatcg ttacgtttac aaggtccctt    540
tcccagtcgc ttgttcagca gggcatacgg gtcaatgcag tggcaccggg tcccatttgg    600
acaccgctta tcccggccag ctttgccgca aaagacgtgg aagtgtttgg ttcagacgtg    660
ccgatggaac gcccggggca gccggtcgaa gtggcgccaa gctatctata ccttgccagc    720
gacgattcca catacgtcac agggcagacg attcacgtca atggcggaac aattgtgaac    780
ggataataaa aagccaatcc ttgaaggatt ggcttattcg ctctgcttga gcgctgcata    840
ttctttagag agcgtaagaa acgcatcttt atctttttcg tccaaggctt tgttaatttg    900
gtccgtcagc atggcaagcc gacggttata caaggattca tcgagcacca tttgaatgta    960
aatatccgtc attgtgacat cgaattcttt tgttttttgc gtgttgcggg acttcatgag    1020
ctcagtgtac gattttttct ctttcatcgg atttgatccc gtataccgtt cgtatagcat    1080
acattatacg aagttatgcc atagtgactg gcgatgctgt cggaatggac gacggcaata    1140 gttacccttta ttatcaagat aagaaagaaa aggattttttc gctacgctca aatcctttaa    1200
aaaaacacaa aagaccacat ttttaatgt ggtcttttat tcttcaacta agcacccat    1260 tagttcaaca aacgaaaatt ggataaagtg ggatattttt aaaatatata tttatgttac    1320
agtaatattg acttttaaaa aaggattgat tctaatgaag aaagcagaca agtaagcctc    1380
ctaaattcac tttagataaa aatttaggag gcatatcaaa tgaactttaa taaaattgat    1440
ttagacaatt ggaagagaaa agagatattt aatcattatt tgaaccaaca aacgactttt    1500
agtataacca cagaaattga tattagtgtt ttataccgaa acataaaaca agaaggatat    1560
aaattttacc ctgcatttat tttcttagtc acaagggtga taaactcaaa tacagctttt    1620
agaactggtt acaatagcga cggagagtta ggttattggg ataagttaga gccactttat    1680 acaattttttg atggtgtatc taaaacattc tctggtatttt ggactcctgt aaagaatgac    1740
ttcaaagagt tttatgattt ataccttttct gatgtagaga aatataatgg ttcggggaaa    1800
ttgtttccca aaacacctat acctgaaaat gcttttttctc tttctattat tccatggact    1860
tcatttactg ggtttaactt aaatatcaat aataatagta attaccttct acccattatt    1920
acagcaggaa aattcattaa taaaggtaat tcaatatatt taccgctatc tttacaggta    1980
catcattctg tttgtgatgg ttatcatgca ggattgttta tgaactctat tcaggaattg    2040
tcagataggc ctaatgactg gctttttataa tatgagataa tgccgactgt acttttttaca    2100 gtcggttttc taaaacgata cattaatagg tacgaaaaag caactttttt tgcgcttaaa    2160
accagtcata ccaataaata acttcgtata gcatacatta tacgaacggt attcagaacg    2220
ctcggttgcc gccgggcgtt ttttatgcag caatggcaag aacgtcccgg ggagctccta    2280
acttataggg gtaacactta aaaagaatc aataacgata gaaaccgctc ctaaagcagg    2340
tgcatttttt cctaacgaag aaggcaatag ttcacattta ttgtctaaat gagaatggac    2400
tctagaagaa acttcgtttt taatcgtatt taaacaatg ggatgagatt caattatatg    2460
atttctcaag ataacagctt ctatatcaaa tgtattaagg atattggtta atccaattcc    2520
```

-continued

```
gatataaaag ccaaagtttt gaagtgcatt taacatttct acatcatttt tatttgcgcg    2580
ttccacaatc tcttttcgag aaatattctt ttcttcttta gagagcgaag ccagtaacgc    2640
tttttcagaa gcatataatt cccaacagcc tcgatttcca cagctgcatt tgggtccatt    2700
aaaatctatc gtcatatgac ccatttcccc agaaaaaccc tgaacacctt tatacaattc    2760
gttgttaata acaagtccag ttccaattcc gatattaata ctgatgtaaa cgatgttttc    2820 atagttttt gtcataccaa atacttttc accgtatgct cctgcattag cttcattttc     2880
aacaaaaacc ggaacattaa actcactctc aattaaaaac tgcaaatctt tgatattcca    2940
atttaagtta ggcatgaaaa taatttgctg atgacgatct acaaggcctg aacacaaat    3000 tcctattccg actagaccat aaggggactc aggcatatgg gttacaaaac catgaataag    3060
tgcaaataaa atctcttta cttcactagc ggaagaacta acaagtcag aagtcttctc      3120 gagaataata tttccttcta agtcggttag aattccgtta agatagtcga ctcctatatc    3180
aataccaatc gagtagcctg cattcttatt aaaacaagc attacaggtc ttctgccgcc     3240
tctagattgc cctgccccaa tttcaaaaat aaaatctttt tcaagcagtg tatttacttg    3300
agaggagaca gtagacttgt ttaatcctgt aatctcagag agagttgccc tggagacagg    3360
ggagttcttc aaaatttcat ctaatattaa ttttgattc atttttta ctaaagcttg        3420 atctgcaatt tgaataataa ccactccttt gtttatccac cgaactaagt tggtgttttt    3480
tgaagcttga attagatatt taaagtatc atatctaata ttataactaa attttctaaa     3540
aaaaacattg aaataaacat ttattttgta tatgatgaga taaagttagt ttattggata    3600
aacaaactaa ctcaattaag atagttgatg gataaacttg ttcacttaaa tcaaaggggg    3660
aaatgacaaa tggtccaaac tagtgatatc taaaaatcaa aggggaaat gggatccatg      3720 agtcagaaaa cagacgcacc tttagaatcg tatgaagtga acggcgcaac aattgccgtg    3780
ctgccagaag aaatagacgg caaaatctgt tccaaaatta ttgaaaaga ttgcgtgttt    3840 tatgtaaaca tgaagccgct gcaaattgtc gacagaagct gccgattttt tggatcaagc    3900
tatgcgggaa gaaaagcagg aacttatgaa gtgacaaaaa tttcacacaa gccgccgatc   3960
atggtggacc cttcgaacca aatcttttta ttccctacac tttcttcgac aagaccccaa    4020
tgcggctgga tttcccatgt gcatgtaaaa gaattcaaag cgactgaatt cgacgatacg    4080
gaagtgacgt tttccaatgg gaaaacgatg gagctgccga tctcttataa ttcgttcgag    4140
aaccaggtat accgaacagc gtggctcaga accaaattcc aagacagaat cgaccaccgc    4200
gtgccgaaaa gacaggaatt tatgctgtac ccgaaagaag agcggacgaa gatgattat    4260 gatttatt tgcgtgagct cggggaacgg tattagaaaa ataggaagga gctgaccgaa     4320
cagggcagct cctttcataa agctatgccg tcggaattcc tccggtgatg ccatatacct    4380
gagatgtcac atagcttgaa ttctctgaag ctagaaatac ataaacatcg gccaattcca    4440
ctggctgccc agcgcgattt aatgagctg gcggcgtgcc ttgtccgaat ttcgggatgt     4500
tttccgtcgg ctgtccgccg gaaatttgca gcggtgtcca aattggtccg ggcgcaactg    4560
aatttact                                                            4568
```

<210> SEQ ID NO 23
<211> LENGTH: 25
<212> TYPE: DNA
<213> ORGANISM: Artificial Sequence
<220> FEATURE:
<223> OTHER INFORMATION: Synthetic DNA

<400> SEQUENCE: 23
gggacaagga atagtaagcc ggcaa                                          25

<210> SEQ ID NO 24
<211> LENGTH: 56
<212> TYPE: DNA
<213> ORGANISM: Artificial Sequence
<220> FEATURE:
<223> OTHER INFORMATION: Synthetic DNA

<400> SEQUENCE: 24
tcctgtgtga aattgttatc cgctcctaca tactctctgt agcagaggta gcttga       56

<210> SEQ ID NO 25
<211> LENGTH: 59
<212> TYPE: DNA
<213> ORGANISM: Artificial Sequence
<220> FEATURE:
<223> OTHER INFORMATION: Synthetic DNA

<400> SEQUENCE: 25
tgaagcccgc ctaatgagcg ggcttttttc tgataagaac tgcaaaagct gcggattat    59

<210> SEQ ID NO 26
<211> LENGTH: 33
<212> TYPE: DNA
<213> ORGANISM: Artificial Sequence
<220> FEATURE:
<223> OTHER INFORMATION: Synthetic DNA

<400> SEQUENCE: 26
ccaccctata gataaatttt tcggctgcca tat                                 33

<210> SEQ ID NO 27
<211> LENGTH: 36
<212> TYPE: DNA
<213> ORGANISM: Artificial Sequence
<220> FEATURE:
<223> OTHER INFORMATION: Synthetic DNA

<400> SEQUENCE: 27
agagtatgta ggagcggata acaatttcac acagga                              36

<210> SEQ ID NO 28
<211> LENGTH: 57
<212> TYPE: DNA
<213> ORGANISM: Artificial Sequence
<220> FEATURE:
<223> OTHER INFORMATION: Synthetic DNA

<400> SEQUENCE: 28
aaagaaatga catgattttg catgtgtaca ttcctctctt acctataatg gtaccgc       57

<210> SEQ ID NO 29
<211> LENGTH: 55
<212> TYPE: DNA
<213> ORGANISM: Artificial Sequence
<220> FEATURE:
<223> OTHER INFORMATION: Synthetic DNA

<400> SEQUENCE: 29
aggtaagaga ggaatgtaca catgcaaaat catgtcattt ctttagcatc agcag         55

<210> SEQ ID NO 30
<211> LENGTH: 55
<212> TYPE: DNA

```
<213> ORGANISM: Artificial Sequence
<220> FEATURE:
<223> OTHER INFORMATION: Synthetic DNA

<400> SEQUENCE: 30
cccgctcatt aggcgggctt catcattact gaaacggaac gataaactgt tcgcg          55

<210> SEQ ID NO 31
<211> LENGTH: 24
<212> TYPE: DNA
<213> ORGANISM: Artificial Sequence
<220> FEATURE:
<223> OTHER INFORMATION: Synthetic DNA

<400> SEQUENCE: 31
cgtatccgat ttgggtgagt gtga                                             24

<210> SEQ ID NO 32
<211> LENGTH: 28
<212> TYPE: DNA
<213> ORGANISM: Artificial Sequence
<220> FEATURE:
<223> OTHER INFORMATION: Synthetic DNA

<400> SEQUENCE: 32
tgatgtcaat ctaatgcctc cttactgg                                         28

<210> SEQ ID NO 33
<211> LENGTH: 4313
<212> TYPE: DNA
<213> ORGANISM: Artificial Sequence
<220> FEATURE:
<223> OTHER INFORMATION: Synthetic DNA

<400> SEQUENCE: 33
cgtatccgat ttgggtgagt gtgacaatca atccagcacc gcttggagaa agtccaattg      60
ccttactaat taatccgacc aagggttgtg catagtaaag attagcaaca atgataccgc     120
atgcagttgc gagaagaagg gttaaactgg gtgaaatcct ctgacctgct tgtttgtttc     180
cattagccat atgaatgaac tcctttttaa gtggtttttt gagtgtaatc atgacttctc     240
acaagtgatt ttataaactg aacgttcagt ttcgtcgatt aataaaaata atatactaaa     300
cgttcagttt tgtaaatgga tttctgtttt ctttttttat tcaatttaag tatactgaac     360
gtatagttta tattgcggga aggaatgatt tatgtgcaga gtaaacgagg cggccgcgt      420 gatgaaggaa cgcataaggc gattctctct gcagcctatg acctattgct ggaaaaaggc     480
ttcgatgcgg tgacagtcga taaaattgcc gagcgtgcga agtgagtaa agcaacgatt     540 tataaatggt ggtctaacaa ggctgccgtt atcatggaca gctttctttc gaccgcgacg     600
gacaggctgc ctgtgcctga tacagggtcg tcagtacaag atatagtaac ccacgccacg     660
aatttagcta ggttttttgac aagccgggaa ggaaccgtta ttaaggaatt aataggtgca     720
gggcagttgg atgaaaaatt ggcagaagaa tatcgcacgc gatttttcca gcctcgccgc     780
ctccaagcga aaggccttct agaaaaggga attcagaaag gtgaattgag agagaatctt     840
gatattgaag taagcataga tctcatttac ggaccaattt tctatcgtct gcttataaca     900
ggggatgagg tgaatgattc ctatgtgcgt gatttggtga tgaatgcgtt taagggagtt     960
caagctacct ctgctacaga gagtatgtag gagcggataa caatttcaca caggaaacag    1020
ctatgaccat gattacgaat tcgagctcgg tacccgggga tcctctagag attgtaccgt    1080
tcgtatagca tacattatac gaagttatcg attttcgttc gtgaatacat gttataataa    1140
```

```
ctataactaa taacgtaacg tgactggcaa gagatatttt taaaacaatg aataggttta    1200
cacttacttt agttttatgg aaatgaaaga tcatatcata tataatctag aataaaatta    1260
actaaaataa ttattatcta gataaaaaat ttagaagcca atgaaatcta taaataaact    1320
aaattaagtt tatttaatta acaactatgg atataaaata ggtactaatc aaaatagtga    1380
ggaggatata tttgaataca tacgaacaag ttaataaagt gaaaaaaata cttcggaaac    1440
atttaaaaaa taaccttatt ggtacttaca tgtttggatc aggagttgag agtggactaa    1500
aaccaaatag tgatcttgac tttttagtcg tcgtatctga accattgaca gatcaaagta    1560
aagaaatact tatacaaaaa attagaccta tttcaaaaaa aataggagat aaaagcaact    1620
tacgatatat tgaattaaca attattattc agcaagaaat ggtaccgtgg aatcatcctc    1680
ccaaacaaga atttatttat ggagaatggt tacaagagct ttatgaacaa ggatacattc    1740
ctcagaagga attaaattca gatttaacca taatgcttta ccaagcaaaa cgaaaaaata    1800
aaagaatata cggaaattat gacttagagg aattactacc tgatattcca ttttctgatg    1860
tgagaagagc cattatggat tcgtcagagg aattaataga taattatcag gatgatgaaa    1920
ccaactctat attaaactttta tgccgtatga ttttaactat ggacacgggt aaaatcatac    1980
caaaagatat tgcgggaaat gcagtggctg aatcttctcc attagaacat agggagagaa    2040
ttttgttagc agttcgtagt tatcttggag agaatattga atggactaat gaaaatgtaa    2100
atttaactat aaactattta aataacagat taaaaaaatt ataaataact tcgtatagca    2160
tacattatac gaacggtaga atcgtcgact gataggtggt atgttttcgc ttgaactttt    2220
aaatacagcc attgaacata cggttgattt aataactgac aaacatcacc ctcttgctaa    2280
agcggccaag gacgccgccg ccggggctgt ttgcgttctt gccgtgattt cgtgtaccat    2340
tggtttactt attttttttgc caaggctgta atggctgaaa attcttacat ttatttttaca    2400 tttttagaaa tgggcgtgaa aaaaagcgcg cgattatgta aaatataaag tgatagcggt    2460
accattatag gtaagagagg aatgtacaca tgcaaaatca tgtcatttct ttagcatcag    2520
cagcggaaag acgcgctcat attgccgata catttggcag acatggaatc ccgtttcaat    2580
ttttcgatgc gcttatgccg tcagaacgct agaacaggc aatggcggaa ttagttccgg    2640
gcctgtcagc tcatccgtat cttagcggag tggaaaaagc atgctttatg agccatgcgg    2700
tcttatggaa acaagctctt gatgaaggcc tgccgtacat cacagttttt gaagatgatg    2760
tgctgcttgg cgaaggagcc gaaaaatttc tggcagaaga tgcgtggctt caggaaagat    2820
ttgatccgga tacagcattt atcgtgcgct agaaacaat gtttatgcat gtcctgacat    2880
caccgagcgg cgttgccgat tattgtggaa gagcatttcc gttactggaa tctgaacatt    2940
ggggcacagc gggatacatc atctcaagaa aagctatgag atttttcctg atagatttg    3000 ctgcccttcc gccggaaggc ttacatccgg ttgatctgat gatgtttttct gatttctttg    3060 atcgcgaagg aatgccggtg tgccaactga atccggctct tgtgcccag gaacttcatt    3120 acgccaaatt tcatgatcaa aacagcgcac tgggatctct tatcgaacat gatagacttc    3180
tgaaccgcaa acaacagaga cgcgatagcc cggcgaacac atttaaacat agattaattc    3240
gcgctctgac aaaaatctct agagaacgcg aaaaagacg ccaaagacgc gaacagttta    3300
tcgttccgtt tcagtaatga tgaagcccgc ctaatgagcg ggctttttc tgataagaac    3360 tgcaaaagct gcggattata tgacaaattg gttccatcgt acagtgaaat ataagatttt    3420
tgttgctgag cggaatcatc gagggaaaag ttctcttatc ggatgtcgaa aaagaagtca    3480
```

```
ttcaatcgtg aatacataac atcatattat tacattcctt ttcatcgatt ggaacaaggg    3540
ttctatactt caatggaata ccgcaaagtt ggagtattta acaacaggg gaaaatcgat     3600 ggccattatg taggtgtcat ggcaatggaa aaaatacttg caatgtaaac aggcctctaa    3660
agagacctgt tttttaatat ccagatgatt gtctagtttc agcttgggct ctatgaccac    3720
tcccataact gaaatagtct aatatttata ccagaaggga ttgtttatat aaataaaagt    3780
ttatataatg acggggggcgc taaggaaacg cggggagcga ctcaggtttt cgtttcaaag   3840
ttttgatcct taagatatac ggagcgctac atatggaaac gtaaaggga atgtataatc     3900 atttggcgtg tatataacga tttgcttata tattgatttg ggaaggagga gctcatatga    3960
cgattgatgt tgcggcgatg actcgttgtt tgaaaacact tagtgatcaa actaggctta    4020
tcatgatgag attatttctt gaacaagaat attgtgtctg tcaattggtt gatatgttcg    4080
aaatgagcca gcccgccata agccagcatt tgcggaaatt aaaaaacgca ggttttgtga    4140
atgaggacag aagaggccaa tggcgttatt attcaataaa tggttcctgt cctgagtttg    4200
atacattgca attgatctta catcaaattg atcaagagga tgaattgtta aaccatatca    4260
aacaaaagaa aactcaagcg tgttgccagt aaggaggcat tagattgaca tca           4313

<210> SEQ ID NO 34
<211> LENGTH: 59
<212> TYPE: DNA
<213> ORGANISM: Artificial Sequence
<220> FEATURE:
<223> OTHER INFORMATION: Synthetic DNA

<400> SEQUENCE: 34
tgaagcccgc ctaatgagcg ggcttttta agcttggcgt aatcatggtc atagctgtt      59

<210> SEQ ID NO 35
<211> LENGTH: 56
<212> TYPE: DNA
<213> ORGANISM: Artificial Sequence
<220> FEATURE:
<223> OTHER INFORMATION: Synthetic DNA

<400> SEQUENCE: 35
ctgtgtgaaa ttgttatccg ctcccagcct ttcttattaa aaccactttg tcagcc         56

<210> SEQ ID NO 36
<211> LENGTH: 7781
<212> TYPE: DNA
<213> ORGANISM: Artificial Sequence
<220> FEATURE:
<223> OTHER INFORMATION: Synthetic DNA

<400> SEQUENCE: 36
tgaagcccgc ctaatgagcg ggcttttta agcttggcgt aatcatggtc atagctgttt      60
cctgtgtgaa attgttatcc gctcacaatt ccacacaaca tacgagccgg aagcataaag    120
tgtaaagcct ggggtgccta atgagtgagc taactcacat taattgcgtt gcgctcactg    180
cccgctttcc agtcgggaaa cctgtcgtgc cagctgcatt aatgaatcgg ccaacgcgcg    240
gggagaggcg gtttgcgtat tgggcgctct tccgcttcct cgctcactga ctcgctgcgc    300
tcggtcgttc ggctgcggcg agcggtatca gctcactcaa aggcggtaat acggttatcc    360
acagaatcag gggataacgc aggaaagaac atgtgagcaa aaggccagca aaaggccagg    420
aaccgtaaaa aggccgcgtt gctggcgttt ttccataggc tccgcccccc tgacgagcat    480
cacaaaaatc gacgctcaag tcagaggtgg cgaaacccga caggactata aagataccag    540
```

```
gcgtttcccc ctggaagctc cctcgtgcgc tctcctgttc cgaccctgcc gcttaccgga      600
tacctgtccg cctttctccc ttcgggaagc gtggcgcttt ctcatagctc acgctgtagg      660
tatctcagtt cggtgtaggt cgttcgctcc aagctgggct gtgtgcacga accccccgtt      720
cagcccgacc gctgcgcctt atccggtaac tatcgtcttg agtccaaccc ggtaagacac      780
gacttatcgc cactggcagc agccactggt aacaggatta gcagagcgag gtatgtaggc      840
ggtgctacag agttcttgaa gtggtggcct aactacggct acactagaag aacagtattt      900
ggtatctgcg ctctgctgaa gccagttacc ttcggaaaaa gagttggtag ctcttgatcc      960
ggcaaacaaa ccaccgctgg tagcggtggt ttttttgttt gcaagcagca gattacgcgc     1020
agaaaaaaag gatctcaaga gatcctttg atcttttcta cggggtctga cgctcagtgg     1080
aacgaaaact cacgttaagg gattttggtc atgagattat caaaaaggat cttcacctag     1140
atccttttaa attaaaaatg aagttttaaa tcaatctaaa gtatatatga gtaaacttgg     1200
tctgacagtt accaatgctt aatcagtgag gcacctatct cagcgatctg tctatttcgt     1260
tcatccatag ttgcctgact ccccgtcgtg tagataacta cgatacggga gggcttacca     1320
tctggcccca gtgctgcaat gataccgcga gacccacgct caccggctcc agatttatca     1380
gcaataaacc agccagccgg aagggccgag cgcagaagtg gtcctgcaac tttatccgcc     1440
tccatccagt ctattaattg ttgccgggaa gctagagtaa gtagttcgcc agttaatagt     1500
ttgcgcaacg ttgttgccat tgctacaggc atcgtggtgt cacgctcgtc gtttggtatg     1560
gcttcattca gctccggttc ccaacgatca aggcgagtta catgatcccc catgttgtgc     1620
aaaaaagcgg ttagctcctt cggtcctccg atcgttgtca gaagtaagtt ggccgcagtg     1680
ttatcactca tggttatggc agcactgcat aattctctta ctgtcatgcc atccgtaaga     1740
tgcttttctg tgactggtga gtactcaacc aagtcattct gagaatagtg tatgcggcga     1800
ccgagttgct cttgcccggc gtcaatacgg gataataccg cgccacatag cagaacttta     1860
aaagtgctca tcattggaaa acgttcttcg ggcgaaaac tctcaaggat cttaccgctg     1920
ttgagatcca gttcgatgta acccactcgt gcacccaact gatcttcagc atcttttact     1980
ttcaccagcg tttctgggtg agcaaaaaca ggaaggcaaa atgccgcaaa aaagggaata     2040
agggcgacac ggaaatgttg aatactcata ctcttccttt ttcaatatta ttgaagcatt     2100
tatcagggtt attgtctcat gagcggatac atatttgaat gtatttagaa aaataaacaa     2160
ataggggttc cgcgcacatt tccccgaaaa gtgccacctg acgtctaaga accattatt     2220 atcatgacat taacctataa aaataggcgt atcacgaggc cctttcgtct cgcgcgtttc     2280
ggtgatgacg gtgaaaacct ctgacacatg cagctcccgg agacggtcac agcttgtctg     2340
taagcggatg ccgggagcag acaagcccgt cagggcgcgt cagcgggtgt tggcgggtgt     2400
cggggctggc ttaactatgc ggcatcagag cagattgtac tgagagtgca ccatatgcgg     2460
tgtgaaatac cgcacagatg cgtaaggaga aaataccgca tcaggcgcca ttcgccattc     2520
aggctgcgca actgttggga agggcgatcg gtgcgggcct cttcgctatt acgccagctg     2580
gcgaaggggg gatgtgctgc aaggcgatta agttgggtaa cgccagggtt ttcccagtca     2640
cgacgttgta aaacgacggc cagtgaattc cttaaggaac gtacagacgg cttaaaagcc     2700
tttaaaaacg ttttttaaggg gtttgtagac aaggtaaagg ataaaacagc acaattccaa     2760 gaaaacacg atttagaacc taaaagaac gaatttgaac taactcataa ccgagaggta     2820 aaaaagaac gaagtcgaga tcagggaatg agtttataaa ataaaaaaag cacctgaaaa     2880
```

```
ggtgtctttt tttgatggtt ttgaacttgt tctttcttat cttgatacat atagaaataa   2940
cgtcattttt attttagttg ctgaaaggtg cgttgaagtg ttggtatgta tgtgttttaa   3000
agtattgaaa acccttaaaa ttggttgcac agaaaaaccc catctgttaa agttataagt   3060
gactaaacaa ataactaaat agatgggggt ttcttttaat attatgtgtc ctaatagtag   3120
catttattca gatgaaaaat caagggtttt agtggacaag acaaaaagtg gaaaagtgag   3180
accatggaga gaaagaaaaa tcgctaatgt tgattacttt gaacttctgc atattcttga   3240
atttaaaaag gctgaaagag taaaagattg tgctgaaata ttagagtata acaaaatcg    3300
tgaaacaggc gaaagaaagt tgtatcgagt gtggttttgt aaatccaggc tttgtccaat   3360
gtgcaactgg aggagagcaa tgaaacatgg cattcagtca caaaggttg ttgctgaagt    3420
tattaaacaa aagccaacag ttcgttggtt gtttctcaca ttaacagtta aaaatgttta   3480
tgatggcgaa gaattaaata gagtttgtc agatatggct caaggatttc gccgaatgat    3540
gcaatataaa aaaattaata aaatctgt tggttttatg cgtgcaacgg aagtgacaat     3600
aaataataaa gataattctt ataatcagca catgcatgta ttggtatgtg tggaaccaac   3660
ttattttaag aatacagaaa actacgtgaa tcaaaaacaa tggattcaat tttggaaaaa   3720
ggcaatgaaa ttagactatg atccaaatgt aaaagttcaa atgattcgac cgaaaaataa   3780
atataaatcg gatatacaat cggcaattga cgaaactgca aaatatcctg taaggatac    3840
ggatttttatg accgatgatg aagaaaagaa tttgaaacgt tgtctgatt tggaggaagg   3900
tttacaccgt aaaaggttaa tctcctatgg tggtttgtta aaagaaatac ataaaaatt    3960
aaaccttgat gacacagaag aaggcgattt gattcataca gatgatgacg aaaaagccga   4020
tgaagatgga ttttctatta ttgcaatgtg gaattgggaa cggaaaaatt attttattaa   4080
agagtagttc aacaaacggg ccagtttgtt gaagattaga tgctataatt gttattaaaa   4140
ggattgaagg atgcttagga agacgagtta ttaatagctg aataagaacg gtgctctcca   4200
aatattctta tttagaaaag caaatctaaa attatctgaa aagggaatga gaatagtgaa   4260
tggaccaata ataatgacta gagaagaaag aatgaagatt gttcatgaaa ttaaggaacg   4320
aatattggat aaatatgggg atgatgttaa ggctattggt gtttatgct ctcttggtcg    4380
tcagactgat gggccctatt cggatattga tgatgatgtgt gtcatgtcaa cagaggaagc   4440
agagttcagc catgaatgga caaccggtga gtggaaggtg gaagtgaatt ttgatagcga   4500
agagattcta ctagattatg catctcaggt ggaatcagat tggccgctta cacatggtca   4560
atttttctct attttgccga tttatgattc aggtggatac ttagagaaag tgtatcaaac   4620
tgctaaatcg gtagaagccc aaacgttcca cgatgcgatt tgtgccctta tcgtagaaga   4680
gctgtttgaa tatgcaggca aatggcgtaa tattcgtgtg caaggaccga caacatttct   4740
accatccttg actgtacagg tagcaatggc aggtgccatg ttgattggtc tgcatcatcg   4800
catctgttat acgacgagcg cttcggtctt aactgaagca gttaagcaat cagatcttcc   4860
ttcaggttat gaccatctgt gccagttcgt aatgtctggt caacttttccg actctgagaa   4920
acttctggaa tcgctagaga atttctggaa tgggattcag gagtggacag aacgacacgg   4980
atatatagtg gatgtgtcaa aacgcatacc attttgaacg atgacctcta ataattgtta   5040
atcatgttgg ttacgtattt attaacttct cctagtatta gtaattatca tggctgtcat   5100
ggcgcattaa cggaataaag ggtgtgctta atcgggcca ttttgcgtaa taagaaaaag    5160
gattaattat gagcgaattg aattaataat aaggtaatag atttacatta gaaaatgaaa   5220
ggggatttta tgcgtgagaa tgttacagtc tatcccggca ttgccagtcg gggatattaa   5280
```

```
aaagagtata ggttttatt gggataaagt aggtttcact ttggttcacc atgaagatgg      5340
attcgcagtt ctaatgtgta atgaggttcg gattcatcta tgggaggcaa gtgatgaagg      5400
ctggcgcctc gtagtaatga ttcaccggtt tgtacaggtg cggagtcgtt tattgctggt      5460
actgctagtt gccgcattga agtagaggga attgatgaat tatatcaaca tattaagcct      5520
ttgggcattt tgcaccccaa tacatcatta aaagatcagt ggtgggatga acgagacttt      5580
gcagtaattg atcccgacaa caatttgatt agcttttttc aacaaataaa aagctaaaat      5640
ctattattaa tctgttcagc aatcgggcgc gattgctgaa taaaagatac gagagacctc      5700
tcttgtatct ttttatttt gagtggtttt gtccgttaca ctagaaaacc gaaagacaat      5760
aaaaatttta ttcttgctga gtctggcttt cggtaagcta gacaaaacgg acaaaataaa      5820
aattggcaag ggtttaaagg tggagatttt ttgagtgatc ttctcaaaaa atactacctg      5880
tcccttgctg atttttaaac gagcacgaga gcaaaccccc cctttgctga ggtggcagag      5940
ggcaggtttt tttgtttctt ttttctcgta aaaaaagaa aggtcttaaa ggttttatgg      6000
ttttggtcgg cactgccgcg cctcgcagag cacacacttt atgaatataa agtatagtgt      6060
gttatacttt acttggaagt ggttccggaa agagcgaaa atgcctcaca tttgtgccac      6120
ctaaaaagga gcgatttaca tatgagttat gcagtttgta aatgcaaaa agtgaaatca      6180 gctggactaa aaggcatgca atttcataat caaagagagc gaaaaagtag aacgaatgat      6240
gatattgacc atgagcgaac acgtgaaaat tatgatttga aaatgataa aatattgat      6300 tacaacgaac gtgtcaaaga aattattgaa tcacaaaaaa caggtacaag aaaaacgagg      6360
aaagatgctg ttcttgtaaa tgagttgcta gtaacatctg accgagattt ttttgagcaa      6420
ctggatcctg ataggtggta tgttttcgct tgaactttta aatacagcca ttgaacatac      6480
ggttgattta ataactgaca acatcaccc tcttgctaaa gcggccaagg acgccgccgc      6540
cggggctgtt tgcgttcttg ccgtgatttc gtgtaccatt ggtttactta ttttttgcc      6600 aaggctgtaa tggctgaaaa ttcttacatt tattttacat ttttagaaat gggcgtgaaa      6660
aaaagcgcgc gattatgtaa aatataaagt gatagcggta ccattatagg taagagagga      6720
atgtacacat gccgtctgaa gcttttagac gccatagagc ctatcgcgaa aataaacttc      6780
aaccgttagt ctctgtttta atctgcgctt ataacgtgga aaaatatttt gcccaatcac      6840
tggcagcggt tgtgaatcag acatggagaa acctggatat tcttatcgtc gatgatggct      6900
caacagatgg aacacttgct attgcccaaa gatttcaaga acaggatggc agaattcgca      6960
tcttagcaca gccgcgcaat tctggccttaa ttccgtcatt aaacatcgga ttagatgaac      7020
tggcgaaaag cggcggaggc ggagaatata tcgctagaac agatgccgat gatattgctg      7080
ccccggattg gattgaaaaa atcgttggcg aaatggaaaa agatagatca atcatcgcaa      7140
tgggagcgtg gcttgaagtg ttaagcgaag aaaaagatgg caatagactg gctcgccatc      7200
atgaacatgg aaaatctgg aaaaaaccga caagacatga agatattgcc gatttctttc      7260
cgtttggcaa tccgattcat aataacacaa tgatcatgag acgcagcgtc attgatggcg      7320
gacttagata taacacagaa cgcgattggg cggaagatta ccagttttgg tacgatgttt      7380
ctaaactggg aagacttgca tattatccgg aagcgctggt gaaatatcgc cttcatgcta      7440
atcaagtctc aagcaaatat agcatcagac agcatgaaat tgcacaaggc atccagaaaa      7500
cagcgcgcaa cgattttctt caaagcatgg gatttaaaac aagatttgat tctctggaat      7560
accgccagat caaagcagtt gcgtatgaac tgcttgaaaa acatctgccg gaagaagatt      7620
```

```
ttgaaagagc aagacgcttt ctttaccaat gttttaaacg cacagataca ttaccggctg     7680
gcgcctggct ggattttgca gcggatggaa gaatgagacg cttatttaca ctgcgccagt     7740
actttggaat cctgcataga ctgctgaaaa accgctaatg a                         7781
```

<210> SEQ ID NO 37
<211> LENGTH: 33
<212> TYPE: DNA
<213> ORGANISM: Artificial Sequence
<220> FEATURE:
<223> OTHER INFORMATION: Synthetic DNA

<400> SEQUENCE: 37

```
ggctttcgtt gtcttgtgtt caagaaattt cca                                  33
```

<210> SEQ ID NO 38
<211> LENGTH: 56
<212> TYPE: DNA
<213> ORGANISM: Artificial Sequence
<220> FEATURE:
<223> OTHER INFORMATION: Synthetic DNA

<400> SEQUENCE: 38

```
ctgtgtgaaa ttgttatccg ctcccagcct ttcttattaa aaccactttg tcagcc         56
```

<210> SEQ ID NO 39
<211> LENGTH: 54
<212> TYPE: DNA
<213> ORGANISM: Artificial Sequence
<220> FEATURE:
<223> OTHER INFORMATION: Synthetic DNA

<400> SEQUENCE: 39

```
aagcccgcct aatgagcggg cttttttatc ataaagatcc agccttttg cgct            54
```

<210> SEQ ID NO 40
<211> LENGTH: 32
<212> TYPE: DNA
<213> ORGANISM: Artificial Sequence
<220> FEATURE:
<223> OTHER INFORMATION: Synthetic DNA

<400> SEQUENCE: 40

```
ctaaagccca agtcacaata tattgatcgc ct                                   32
```

<210> SEQ ID NO 41
<211> LENGTH: 51
<212> TYPE: DNA
<213> ORGANISM: Artificial Sequence
<220> FEATURE:
<223> OTHER INFORMATION: Synthetic DNA

<400> SEQUENCE: 41

```
gttttaataa gaaaggctgg gagcggataa caatttcaca caggaaacag c              51
```

<210> SEQ ID NO 42
<211> LENGTH: 57
<212> TYPE: DNA
<213> ORGANISM: Artificial Sequence
<220> FEATURE:
<223> OTHER INFORMATION: Synthetic DNA

<400> SEQUENCE: 42

```
aaagaaatga catgattttg catgtgtaca ttcctctctt acctataatg gtaccgc        57
```

<210> SEQ ID NO 43
<211> LENGTH: 55
<212> TYPE: DNA
<213> ORGANISM: Artificial Sequence
<220> FEATURE:
<223> OTHER INFORMATION: Synthetic DNA

<400> SEQUENCE: 43
aggtaagaga ggaatgtaca catgcaaaat catgtcattt ctttagcatc agcag        55

<210> SEQ ID NO 44
<211> LENGTH: 55
<212> TYPE: DNA
<213> ORGANISM: Artificial Sequence
<220> FEATURE:
<223> OTHER INFORMATION: Synthetic DNA

<400> SEQUENCE: 44
cccgctcatt aggcgggctt catcattact gaaacggaac gataaactgt tcgcg        55

<210> SEQ ID NO 45
<211> LENGTH: 31
<212> TYPE: DNA
<213> ORGANISM: Artificial Sequence
<220> FEATURE:
<223> OTHER INFORMATION: Synthetic DNA

<400> SEQUENCE: 45
aacctccttg tcttctttcc agtcttatct c                                  31

<210> SEQ ID NO 46
<211> LENGTH: 29
<212> TYPE: DNA
<213> ORGANISM: Artificial Sequence
<220> FEATURE:
<223> OTHER INFORMATION: Synthetic DNA

<400> SEQUENCE: 46
atcacttctc tttctttcac gctcatcct                                     29

<210> SEQ ID NO 47
<211> LENGTH: 3627
<212> TYPE: DNA
<213> ORGANISM: Artificial Sequence
<220> FEATURE:
<223> OTHER INFORMATION: Synthetic DNA

<400> SEQUENCE: 47
aacctccttg tcttctttcc agtcttatct ctaggatgaa attggaggaa gaataacgtg    60
catgtcatta caacacaagt acttttatt ttttgttttt tattgctgat tcactcgata   120
gaaaccttag cctatgcgac aaggctttcc ggagctcgcg ttggatttat tgcgtccgcg   180
ctttctctgt ttaatgtcat ggtcatcgta tccagaatgt cgaatatggt gcagcagccc   240
tttactgggc atttaattga tgatgctgga aaaaacgcac tggcgattgt aggggagcag   300
ttccgctttt taatttcgg atcgacagtc ggcaccattt tgggcattat cctgctcccg   360
tcttttgtcg ctctttttc acgggcgatt attcacttgg cgggcggcgg cggctccgtt   420
tttcaagtat tccgaaaggg attctcgaaa caaggattca aaaatgccct ttcctatttg   480
cgtctgccgt ccatttcata tgtaaaagga tttcatatgc gcttgattcc gaagcgtttg   540
tttgtcatca acatgctgat cacatcgatt tatacgattg gtgtgctttc ggctttatac   600
gcaggccttt tggcgccgga gcgcagcacg acagccgtca tggcttcggg tttgatcaac   660

```
ggaattgcaa cgatgctgct ggctattttt gttgatccta aggtatccgt tcttgctgat      720
gatgtggcaa aaggaaaacg aagctatatc tatttaaaat ggacctctgt cacaatggtc      780
acatcaaggg tggcgggcac actcctcgcc cagctcatgt ttattcccgg ggcctactat      840
atcgcgtggc tgacaaagtg gttttaataa gaaaggctgg gagcggataa caatttcaca      900
caggaaacag ctatgaccat gattacgaat tcgagctcgg tacccgggga tcctctagag      960
ataccgttcg tatagcatac attatacgaa gttatcttga tatggctttt tatatgtgtt     1020
actctacata cagaaaggag gaactaaaca tggccaagtt gaccagtgcc gttccggtgc     1080
tcaccgcgcg cgacgtcgcc ggagcggtcg agttctggac cgaccggctc gggttctccc     1140
gggacttcgt ggaggacgac ttcgccggtg tggtccggga cgacgtgacc ctgttcatca     1200
gcgcggtcca ggaccaggtg gtgcgggaca cacccctggc ctgggtgtgg gtgcgcggcc     1260
tggacgagct gtacgccgag tggtcggagg tcgtgtccac gaacttccgg gacgcctccg     1320
ggccggccat gaccgagatc ggcgagcagc cgtgggggcg ggagttcgcc ctgcgcgacc     1380
cggccggcaa ctgcgtgcac ttcgtggccg aggagcagga ctgaataact tcgtatagca     1440
tacattatac gaacggtaaa tcgtcgactg ataggtggta tgttttcgct tgaactttta     1500
aatacagcca ttgaacatac ggttgattta ataactgaca aacatcaccc tcttgctaaa     1560
gcggccaagg acgccgccgc cggggctgtt tgcgttcttg ccgtgatttc gtgtaccatt     1620
ggtttactta tttttttgcc aaggctgtaa tggctgaaaa ttcttacatt tattttacat     1680
ttttagaaat gggcgtgaaa aaaagcgcgc gattatgtaa aatataaagt gatagcggta     1740
ccattatagg taagagagga atgtacacat gcaaaatcat gtcatttctt tagcatcagc     1800
agcggaaaga cgcgctcata ttgccgatac atttggcaga catggaatcc cgtttcaatt     1860
tttcgatgcg cttatgccgt cagaacgctt agaacaggca atggcggaat tagttccggg     1920
cctgtcagct catccgtatc ttagcggagt ggaaaaagca tgctttatga gccatgcggt     1980
cttatgaaaa caagctcttg atgaaggcct gccgtacatc acagttttg aagatgatgt     2040 gctgcttggc gaaggagccg aaaaatttct ggcagaagat gcgtggcttc aggaaagatt     2100
tgatccggat acagcattta tcgtgcgctt agaaacaatg tttatgcatg tcctgacatc     2160
accgagcggc gttgccgatt attgtggaag agcatttccg ttactggaat ctgaacattg     2220
gggcacagcg ggatacatca tctcaagaaa agctatgaga tttttcctgg atagatttgc     2280
tgcccttccg ccggaaggct tacatccggt tgatctgatg atgtttttctg atttctttga     2340 tcgcgaagga atgccggtgt gccaactgaa tccggctctt tgtgcccagg aacttcatta     2400
cgccaaattt catgatcaaa acagcgcact gggatctctt atcgaacatg atagacttct     2460
gaaccgcaaa caacagagac gcgatagccc ggcgaacaca tttaaacata gattaattcg     2520
cgctctgaca aaaatctcta gagaacgcga aaaagacgc caaagacgcg aacagtttat     2580
cgttccgttt cagtaatgat gaagcccgcc taatgagcgg gcttttttat cataaagatc     2640
cagccttttt gcgcttcctt atttatagtt ccttaatccg cggtcgtaca aaaaatttcc     2700
gaatgggacg aaagcggcga tgaagccggc agctgaccat ttcagcggcc atttgacaga     2760
gaaggttgca taagccaaga caagcaaata caaaatgaac aacccgccgt gaaccgaacc     2820
gacaattgtc accgcaagcg gaaggcctgc ccaatattta agcggcatag cgatgaacaa     2880
caggattaag agtgacattc cttcaataaa acccatcgtg cgaagtcttc cgatcggcgt     2940
gtgcagcata aatcgccctc cttgtggaca cgttttcatt ttatactata aacaatccgg     3000
gggggcatat gacagctttc aaaaaatgtt cggaaaacat tcattttac atgccttttc     3060
```

```
tagggaactg tacttgtcat ttacaaaaat acccgagata atgtgtacaa aatcaaaaaa    3120
gaaggatgtt gaaatgaaac ttgaccagat tgatctgaat atcattgagg agctgaagaa    3180
ggacagccgt ttgtcgatga gggaattagg cagaaaaatt aagctgtcgc ctccatctgt    3240
aacagaacgg gtaagacagc ttgaatcgtt tggcatcatc aagcaataca cgctggaggt    3300
cgaccagaaa aaactggggc ttcccgtttc ctgcattgtg gaagcaaccg ttaaaaacgc    3360
ggattatgag cggttcaaaa gctatattca aacattgccg aatattgaat tttgctaccg    3420
gattgcgggt gcagcctgct atatgctgaa aatcaatgcc gaaagcctcg aagcggtaga    3480
agatttcatt aacaaaacat cgccctacgc gcaaaccgtc actcacgtca ttttctcaga    3540
aattgacacg aaaaacgggc gcggttagag agtgccgcgc gaagtctgtt ataataacag    3600
gatgagcgtg aaagaaagag aagtgat                                        3627
```

<210> SEQ ID NO 48
<211> LENGTH: 35
<212> TYPE: DNA
<213> ORGANISM: Artificial Sequence
<220> FEATURE:
<223> OTHER INFORMATION: Synthetic DNA

<400> SEQUENCE: 48

```
catccagcgt aaaacgttca cgggaataat ctagg                                35
```

<210> SEQ ID NO 49
<211> LENGTH: 50
<212> TYPE: DNA
<213> ORGANISM: Artificial Sequence
<220> FEATURE:
<223> OTHER INFORMATION: Synthetic DNA

<400> SEQUENCE: 49

```
ttatccgctc tggcgcggac ttgtttgttt atatccattc taaatgaagg               50
```

<210> SEQ ID NO 50
<211> LENGTH: 59
<212> TYPE: DNA
<213> ORGANISM: Artificial Sequence
<220> FEATURE:
<223> OTHER INFORMATION: Synthetic DNA

<400> SEQUENCE: 50

```
gcccgcctaa tgagcgggct ttttttaag acgtggactc gttttcagcc tgaaattttt    59
```

<210> SEQ ID NO 51
<211> LENGTH: 29
<212> TYPE: DNA
<213> ORGANISM: Artificial Sequence
<220> FEATURE:
<223> OTHER INFORMATION: Synthetic DNA

<400> SEQUENCE: 51

```
catcccagca gctgatcagg atgaattct                                      29
```

<210> SEQ ID NO 52
<211> LENGTH: 49
<212> TYPE: DNA
<213> ORGANISM: Artificial Sequence
<220> FEATURE:
<223> OTHER INFORMATION: Synthetic DNA

<400> SEQUENCE: 52
acaagtccgc gccagagcgg ataacaattt cacacaggaa acagctatg        49

<210> SEQ ID NO 53
<211> LENGTH: 56
<212> TYPE: DNA
<213> ORGANISM: Artificial Sequence
<220> FEATURE:
<223> OTHER INFORMATION: Synthetic DNA

<400> SEQUENCE: 53
agaaatgaca tgattttgca tgtgtacatt cctctcttac ctataatggt accgct    56

<210> SEQ ID NO 54
<211> LENGTH: 59
<212> TYPE: DNA
<213> ORGANISM: Artificial Sequence
<220> FEATURE:
<223> OTHER INFORMATION: Synthetic DNA

<400> SEQUENCE: 54
ataggtaaga gaggaatgta cacatgcaaa atcatgtcat ttctttagca tcagcagcg   59

<210> SEQ ID NO 55
<211> LENGTH: 57
<212> TYPE: DNA
<213> ORGANISM: Artificial Sequence
<220> FEATURE:
<223> OTHER INFORMATION: Synthetic DNA

<400> SEQUENCE: 55
gcccgctcat taggcgggct tcatcattac tgaaacggaa cgataaactg ttcgcgt    57

<210> SEQ ID NO 56
<211> LENGTH: 26
<212> TYPE: DNA
<213> ORGANISM: Artificial Sequence
<220> FEATURE:
<223> OTHER INFORMATION: Synthetic DNA

<400> SEQUENCE: 56
gccaggaagc cacagcacat catagc        26

<210> SEQ ID NO 57
<211> LENGTH: 35
<212> TYPE: DNA
<213> ORGANISM: Artificial Sequence
<220> FEATURE:
<223> OTHER INFORMATION: Synthetic DNA

<400> SEQUENCE: 57
ttcgttcatt cgttcccgtt tacagaacaa atagc        35

<210> SEQ ID NO 58
<211> LENGTH: 4150
<212> TYPE: DNA
<213> ORGANISM: Artificial Sequence
<220> FEATURE:
<223> OTHER INFORMATION: Synthetic DNA

<400> SEQUENCE: 58
gccaggaagc cacagcacat catagccctg catgcgtttc attcttgtta caatgtcttg    60
cagcgttgtg tcccatgcgt ggccaaggtg aagtctccct gttacgtttg gcggcgggat   120
gacaacagag tatggctctt ttgtctggtc actgcccgct tcaaaaaatt tgcctttag    180 ccaaaaatca tatcggtctt tttcaaccgc tgccggatca tatttcgtcg gcattgtttg   240

```
ttcattcgtt tccatcataa ccctccagca tgtttaaaaa tggctgagaa cgaaaaaga    300
gctcttcatc cctgtaaaag gacgaaaagc tctttcgcgg taccaccttt tttcatgaac   360
tcaatcagtt catgcactta taacggataa cgggtgtttc ccgaatttct ctactcttct   420
ttcaagaaat tatgctcccg ggcgaccttc caatcagaca acataagaag cctttcagca   480
aacggcttct ctctctgcat gcgccttttt tgtactcttc ccgttctaag caggtgtatt   540
tatcagctca ttgtatacat tatttatgtt ctttattata gtaaaagtgt ttttgattcg   600
tcaatcatct tttccaaaaa caccgctttc tatacagatg ggcaggcacc tattgcccaa   660
gtttacatat gatgcttgta aatgcgtaga ggaggatgca ccgtgaagaa acgtttcagc   720
tcttattcgc tgccgccatg ggtaaggcaa attcggcttg tatccgcaca agtgattatt   780
cccattacga ttttcaagg aatcagaacc attttctttc cgacaacctt tgatgttttg    840
ctgctcgcaa tcctaatctt tttagcttgc gcccttcatt tagaatggat ataaacaaac   900
aagtccgcgc cagagcggat aacaatttca cacaggaaac agctatgacc atgattacga   960
attcgagctc ggtacccggg gatcctctag agattgtacc gttcgtatag catacattat  1020
acgaagttat gccatagtga ctggcgatgc tgtcggaatg gacgacggca atagttaccc  1080
ttattatcaa gataagaaag aaaaggattt ttcgctacgc tcaaatcctt taaaaaaaca  1140
caaaagacca cattttttaa tgtggtcttt tattcttcaa ctaaagcacc cattagttca  1200
acaaacgaaa attggataaa gtgggatatt tttaaaatat atatttatgt tacagtaata  1260
ttgactttta aaaaggatt gattctaatg aagaaagcag acaagtaagc ctcctaaatt    1320
cactttagat aaaaatttag gaggcatatc aaatgaactt taataaaatt gatttagaca  1380
attggaagag aaaagagata tttaatcatt atttgaacca acaaacgact tttagtataa  1440
ccacagaaat tgatattagt gttttatacc gaaacataaa acaagaagga tataaatttt  1500
accctgcatt tattttctta gtgacaaggg tgataaactc aaatacagct tttagaactg  1560
gttacaatag cgacggagag ttaggttatt gggataagtt agagccactt tatacaattt  1620
ttgatggtgt atctaaaaca ttctctggta tttggactcc tgtaaagaat gacttcaaag  1680
agttttatga tttatacctt tctgatgtag agaaatataa tggttcgggg aaattgtttc  1740
ccaaaacacc tatacctgaa aatgcttttt ctctttctat tattccatgg acttcattta  1800
ctgggtttaa cttaaatatc aataataata gtaattacct tctacccatt attacagcag  1860
gaaaattcat taataaaggt aattcaatat atttaccgct atctttacag gtacatcatt  1920
ctgtttgtga tggttatcat gcaggattgt ttatgaactc tattcaggaa ttgtcagata  1980
ggcctaatga ctggctttta taatatgaga taatgccgac tgtacttttt acagtcggtt  2040
ttctaacgat acattaatag gtacgaaaaa gcaactttt ttgcgcttaa accagtcat    2100
accaataaat aacttcgtat agcatacatt atacgaacgg tatgataggt ggtatgtttt  2160
cgcttgaact tttaaataca gccattgaac atacggttga tttaataact gacaaacatc  2220
accctcttgc taaagcggcc aaggacgccg ccgccggggc tgtttgcgtt cttgccgtga  2280
tttcgtgtac cattggttta cttatttttt tgccaaggct gtaatggctg aaaattctta  2340
catttatttt acatttttag aaatgggcgt gaaaaaagc gcgcgattat gtaaaatata   2400
aagtgatagc ggtaccatta taggtaagag aggaatgtac acatgcaaaa tcatgtcatt  2460
tctttagcat cagcagcgga aagacgcgct catattgccg atacatttgg cagacatgga  2520
atcccgtttc aattttttcga tgcgcttatg ccgtcagaac gcttagaaca ggcaatggcg  2580
```

-continued

| | |
|---|---|
| gaattagttc cgggcctgtc agctcatccg tatcttagcg gagtggaaaa agcatgcttt | 2640 |
| atgagccatg cggtcttatg gaaacaagct cttgatgaag gcctgccgta catcacagtt | 2700 |
| tttgaagatg atgtgctgct tggcgaagga gccgaaaaat ttctggcaga agatgcgtgg | 2760 |
| cttcaggaaa gatttgatcc ggatacagca tttatcgtgc gcttagaaac aatgtttatg | 2820 |
| catgtcctga catcaccgag cggcgttgcc gattattgtg gaagagcatt ccgttactg | 2880 |
| gaatctgaac attggggcac agcgggatac atcatctcaa gaaaagctat gagattttc | 2940 |
| ctggatagat ttgctgccct ccgccggaa ggcttacatc cggttgatct gatgatgttt | 3000 |
| tctgatttct tgatcgcga aggaatgccg gtgtgccaac tgaatccggc tctttgtgcc | 3060 |
| caggaacttc attacgccaa atttcatgat caaaacagcg cactgggatc tcttatcgaa | 3120 |
| catgatagac ttctgaaccg caaacaacag agacgcgata gcccggcgaa cacatttaaa | 3180 |
| catagattaa ttcgcgctct gacaaaaatc tctagagaac gcgaaaaaag acgccaaaga | 3240 |
| cgcgaacagt ttatcgttcc gtttcagtaa tgatgaagcc cgcctaatga gcgggctttt | 3300 |
| ttttaagacg tggactcgtt ttcagcctga aatttttct cttgttcaat ctgatgaatt | 3360 |
| ttcatcacaa acggctctat gttttttcatt tgccaataag cctttaataa ttgtgtacat | 3420 |
| tcctctttt catgctgtct tttcccagtt tgataaccgt tcagcaccttt gtacatggct | 3480 |
| gccggatatg ccatatagct gagaaaaagg ctgacttccg cttcacgcaa agggaatgat | 3540 |
| ttcgtatatc cataaaacca ttcgacgcat tccggacaag ctttcggaaa gcctctgaac | 3600 |
| atttttgtat aaaagccgag caggtcgttt tgcggcggac cgacagatgc tctttcgaag | 3660 |
| tttgtaaaat atccggtccc ggcatcatta tacagaaaat ggtgtataga caggctgccg | 3720 |
| tggttcatta caacccttga aacgtccttt tcctttgcgg actcatacca gtcctccagc | 3780 |
| cgttccagcg caaagttcac cgcggaaatg gtttcagaaa aataggttat ggcctggagt | 3840 |
| tcaaagggag aaaggtacca ttccttctcc gctctatcca caaactgctc atagaaaatt | 3900 |
| ttatcttgtt cccacttttt tttcgtttgc ccgtaataac gttcaatctc atcacgtcta | 3960 |
| acctttagtt cctgcgcggt tctctcgtga agacgggctg tttctctaaa taaataagca | 4020 |
| tgttttttgat cccgttcttc ctcttggtca aattggagcc aaggcattaa atagtagata | 4080 |
| tctccgtatt gtatgcctgc tgagaaaaac tcaccgctat tgttctgta aacgggaacg | 4140 |
| aatgaacgaa | 4150 |

<210> SEQ ID NO 59
<211> LENGTH: 29
<212> TYPE: DNA
<213> ORGANISM: Artificial Sequence
<220> FEATURE:
<223> OTHER INFORMATION: Synthetic DNA

<400> SEQUENCE: 59

| | |
|---|---|
| cgaaggaatg ccggtgtgcc aactgaatc | 29 |

<210> SEQ ID NO 60
<211> LENGTH: 30
<212> TYPE: DNA
<213> ORGANISM: Artificial Sequence
<220> FEATURE:
<223> OTHER INFORMATION: Synthetic DNA

<400> SEQUENCE: 60

| | |
|---|---|
| cgacctccag cgtgtattgc ttgatgatgc | 30 |

```
<210> SEQ ID NO 61
<211> LENGTH: 30
<212> TYPE: DNA
<213> ORGANISM: Artificial Sequence
<220> FEATURE:
<223> OTHER INFORMATION: Synthetic DNA

<400> SEQUENCE: 61
gggcacagcg ggatacatca tctcaagaaa                                         30

<210> SEQ ID NO 62
<211> LENGTH: 29
<212> TYPE: DNA
<213> ORGANISM: Artificial Sequence
<220> FEATURE:
<223> OTHER INFORMATION: Synthetic DNA

<400> SEQUENCE: 62
tgaaccacgg cagcctgtct atacaccat                                          29
```